(12) United States Patent
McLoughlin et al.

(10) Patent No.: US 10,918,792 B2
(45) Date of Patent: Feb. 16, 2021

(54) HOUSING PART FOR AN AUTO-INJECTOR

(71) Applicants: UCB BIOPHARMA SPRL, Brussels (BE); BESPAK EUROPE LIMITED, Hemel Hempstead (GB)

(72) Inventors: Martin John McLoughlin, Slough (GB); Barry Alan Knight, Slough (GB); Matt Ekman, Hemel Hempstead (GB); Deborah Jane Norris, Hemel Hempstead (GB)

(73) Assignees: USB Biopharma SPRL, Brussels (BE); Bespak Europe Limited, Hemel Hempsead (GB)

( * ) Notice: Subject to any disclaimer, the term of this patent is extended or adjusted under 35 U.S.C. 154(b) by 360 days.

(21) Appl. No.: 15/513,771

(22) PCT Filed: Sep. 21, 2015

(86) PCT No.: PCT/EP2015/071601
§ 371 (c)(1),
(2) Date: Mar. 23, 2017

(87) PCT Pub. No.: WO2016/046131
PCT Pub. Date: Mar. 31, 2016

(65) Prior Publication Data
US 2017/0239419 A1    Aug. 24, 2017

(30) Foreign Application Priority Data

Sep. 26, 2014  (GB) .................................. 1416985.8

(51) Int. Cl.
*A61M 5/20*        (2006.01)
*A61M 5/31*        (2006.01)
(Continued)

(52) U.S. Cl.
CPC ........ *A61M 5/2033* (2013.01); *A61M 5/3137* (2013.01); *A61M 5/31576* (2013.01);
(Continued)

(58) Field of Classification Search
CPC ...... A61M 5/178; A61M 5/20; A61M 5/2033; A61M 5/31; A61M 5/3137;
(Continued)

(56) References Cited

U.S. PATENT DOCUMENTS 4,333,456 A     6/1982  Webb
4,985,000 A *   1/1991  Tengler .............. H01R 13/6585
                                                           439/445
(Continued)

FOREIGN PATENT DOCUMENTS

CN          1913933        2/2007
CN          102917737      2/2013
(Continued)

OTHER PUBLICATIONS

Narhi, Ward and Evans, Ellen; TPV overmolding, Rubber World, vol. 239, Issue 3, (Created: Aug. 7, 2012), pp. 14(3), ISSN: 0035-9572, (First Availible: Sep. 23, 2012) (Year: 2012).*
(Continued)

*Primary Examiner* — Nathan R Price
*Assistant Examiner* — Mark A Igel
(74) *Attorney, Agent, or Firm* — Stoel Rives LLP

(57) ABSTRACT

Provided is a housing part for an auto-injector comprising a shell form body defining inner and outer shell surfaces and comprising a relatively hard or generally incompressible material; an over-coating formed of a relatively softer or more compressible material, the over-coating covering at least part of the outer shell surface of the shell form body; and at least one window defined in the shell form body, wherein the over-coating extends into the at least one
(Continued)

window. Also provided is a housing comprising the housing part, and an auto-injector comprising the housing.

18 Claims, 18 Drawing Sheets

(51) Int. Cl.
  *A61M 5/32* (2006.01)
  *A61M 5/315* (2006.01)
(52) U.S. Cl.
  CPC ........ *A61M 5/3202* (2013.01); *A61M 5/3243* (2013.01); *A61M 2005/3125* (2013.01); *A61M 2205/0216* (2013.01); *A61M 2205/0238* (2013.01)
(58) Field of Classification Search
  CPC ............ A61M 5/31576; A61M 5/3202; A61M 5/3243; A61M 2005/3125; A61M 2205/0216; A61M 2205/0238; A61B 5/150259; G03B 17/563
  See application file for complete search history.

(56) References Cited

U.S. PATENT DOCUMENTS

| | | | | |
|---|---|---|---|---|
| 6,223,733 | B1* | 5/2001 | Busato | F02M 25/0836 123/568.18 |
| 6,305,908 | B1* | 10/2001 | Hermann | A61M 5/14244 417/234 |
| D660,958 | S* | 5/2012 | McLoughlin | D24/113 |
| 2001/0001822 | A1* | 5/2001 | Chambers | A61F 2/1664 606/107 |
| 2002/0127264 | A1* | 9/2002 | Felt | A61B 17/562 424/423 |
| 2003/0050592 | A1* | 3/2003 | Slate | A61M 5/20 604/35 |
| 2004/0035491 | A1* | 2/2004 | Castellano | A61M 5/30 141/27 |
| 2004/0147901 | A1* | 7/2004 | Py | A61M 5/2033 604/506 |
| 2005/0131355 | A1* | 6/2005 | Kirchhofer | A61M 5/3129 604/187 |
| 2006/0184117 | A1* | 8/2006 | Knight | A61M 5/24 604/135 |
| 2007/0068531 | A1 | 3/2007 | Matlock et al. | |
| 2008/0082044 | A1 | 4/2008 | Sharon et al. | |
| 2008/0195056 | A1* | 8/2008 | Bishop | A61M 5/2033 604/218 |
| 2008/0317605 | A1 | 12/2008 | Amley et al. | |
| 2009/0209883 | A1* | 8/2009 | Higgins | A61B 5/150022 600/575 |
| 2010/0016795 | A1* | 1/2010 | McLoughlin | A61M 5/3137 604/134 |
| 2010/0116987 | A1* | 5/2010 | Guichard | A61B 6/145 250/336.1 |
| 2010/0185148 | A1 | 7/2010 | Gillespie, III et al. | |
| 2012/0289905 | A1* | 11/2012 | Julian | A61M 5/20 604/189 |
| 2013/0112521 | A1* | 5/2013 | Ekman | A61M 5/20 192/69.8 |
| 2013/0123710 | A1* | 5/2013 | Ekman | A61M 5/2033 604/198 |
| 2013/0138048 | A1* | 5/2013 | Kemp | A61M 5/2033 604/196 |
| 2013/0138049 | A1* | 5/2013 | Kemp | A61M 5/2033 604/197 |
| 2013/0150801 | A1* | 6/2013 | Ekman | A61M 5/2033 604/198 |
| 2013/0190694 | A1* | 7/2013 | Barrow-Williams | A61M 5/2033 604/198 |
| 2013/0338593 | A1* | 12/2013 | Wozencroft | A61M 5/2033 604/157 |
| 2014/0148763 | A1* | 5/2014 | Karlsson | A61M 5/28 604/198 |
| 2014/0228769 | A1* | 8/2014 | Karlsson | A61M 5/2033 604/197 |
| 2014/0257191 | A1* | 9/2014 | Cowe | A61M 5/20 604/189 |
| 2014/0309591 | A1* | 10/2014 | Holmqvist | A61M 5/20 604/154 |
| 2014/0330215 | A1* | 11/2014 | Kikuchi | A61M 5/20 604/189 |
| 2015/0224262 | A1* | 8/2015 | Jugl | A61M 5/24 604/187 |
| 2017/0312173 | A1* | 11/2017 | Klintenstedt | A61J 1/16 |

FOREIGN PATENT DOCUMENTS

| | | | | |
|---|---|---|---|---|
| CN | 103153367 | | 6/2013 | |
| CN | 103167889 | | 6/2013 | |
| CN | 103533975 | | 1/2014 | |
| CN | 103619378 | | 3/2014 | |
| EP | 1681070 | A1* | 7/2006 | .............. A61M 5/24 |
| EP | 1952835 | | 8/2008 | |
| EP | 1952835 | A1* | 8/2008 | ........ A61M 5/14244 |
| EP | 2080532 | | 7/2009 | |
| GB | 2445090 | | 6/2008 | |
| GB | 2463071 | | 3/2010 | |
| GB | 2466371 | | 6/2010 | |
| GB | 2475917 | | 6/2011 | |
| JP | 3052991 | | 5/1991 | |
| JP | 2012082262 | | 4/2012 | |
| WO | 199855168 | | 12/1998 | |
| WO | WO-9855168 | A1* | 12/1998 | .......... A61M 5/3137 |
| WO | 199965547 | | 12/1999 | |
| WO | WO-9965547 | A1* | 12/1999 | ........ A61M 5/14244 |
| WO | 2002076374 | | 10/2002 | |
| WO | 2005070481 | | 8/2005 | |
| WO | 2007083115 | | 7/2007 | |
| WO | 2011051366 | | 5/2011 | |
| WO | 2011070246 | | 6/2011 | |
| WO | 2011112309 | | 9/2011 | |
| WO | WO-2011112309 | A1* | 9/2011 | .............. B32B 5/26 |
| WO | 2012145685 | | 10/2012 | |
| WO | 2013077800 | | 5/2013 | |
| WO | 2014033141 | | 3/2014 | |

OTHER PUBLICATIONS

Elastomers and Thermoplastics Engineering Design Guide Rubber over-Molding, Mar. 23, 2012 [databaseonline] Minnesota Rubber & Plastics [Retrieved on: Apr. 22, 2019] Retrieved from: Thewaybackmachine, https://web.archive.org/web/20120323021336/ http://www.mnrubber.com/Design_Guide/2-13.html (Year: 2012).*
International Search Report and Written Opinion dated Dec. 10, 2015 for PCT/EP2015/071601.

* cited by examiner

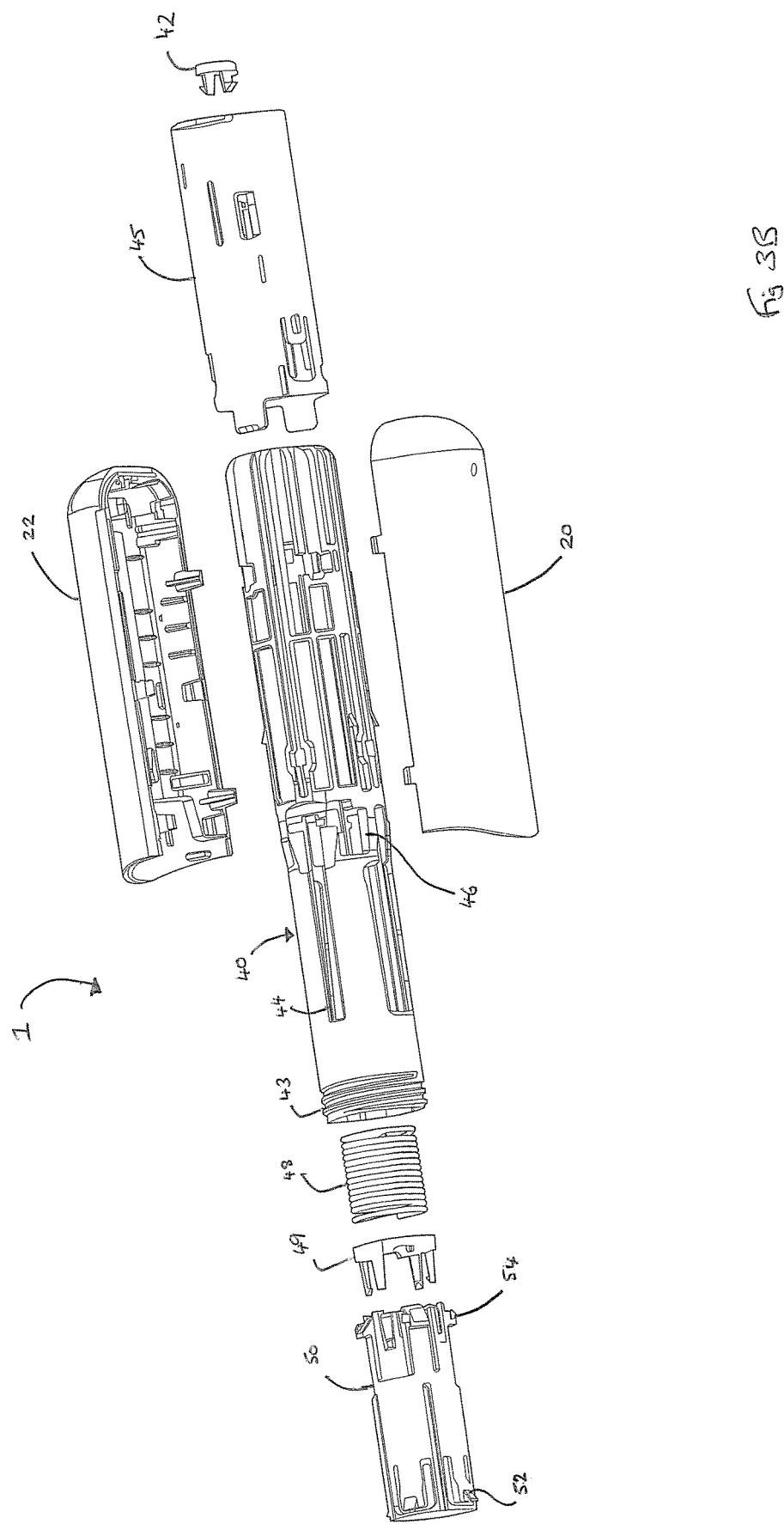

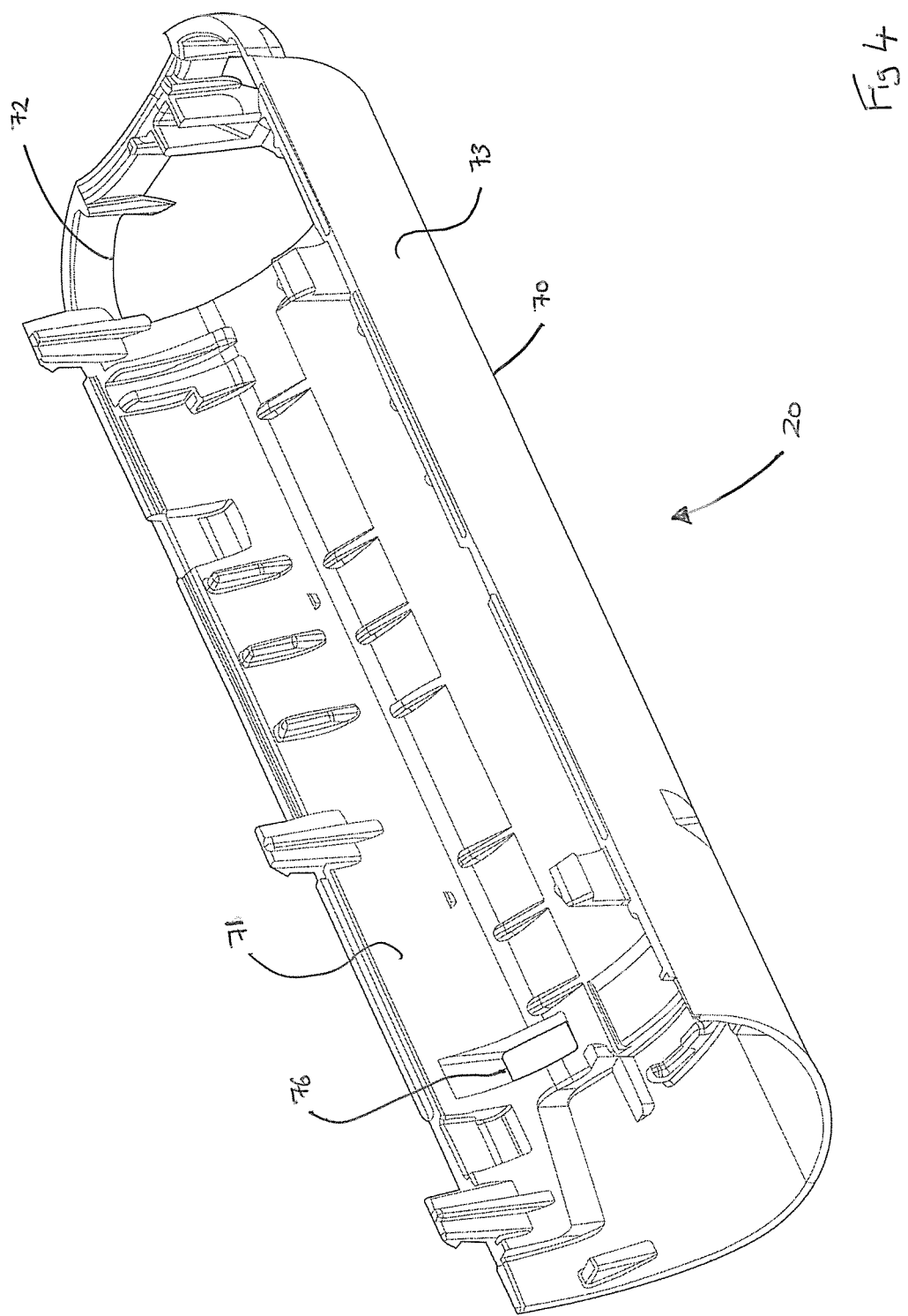

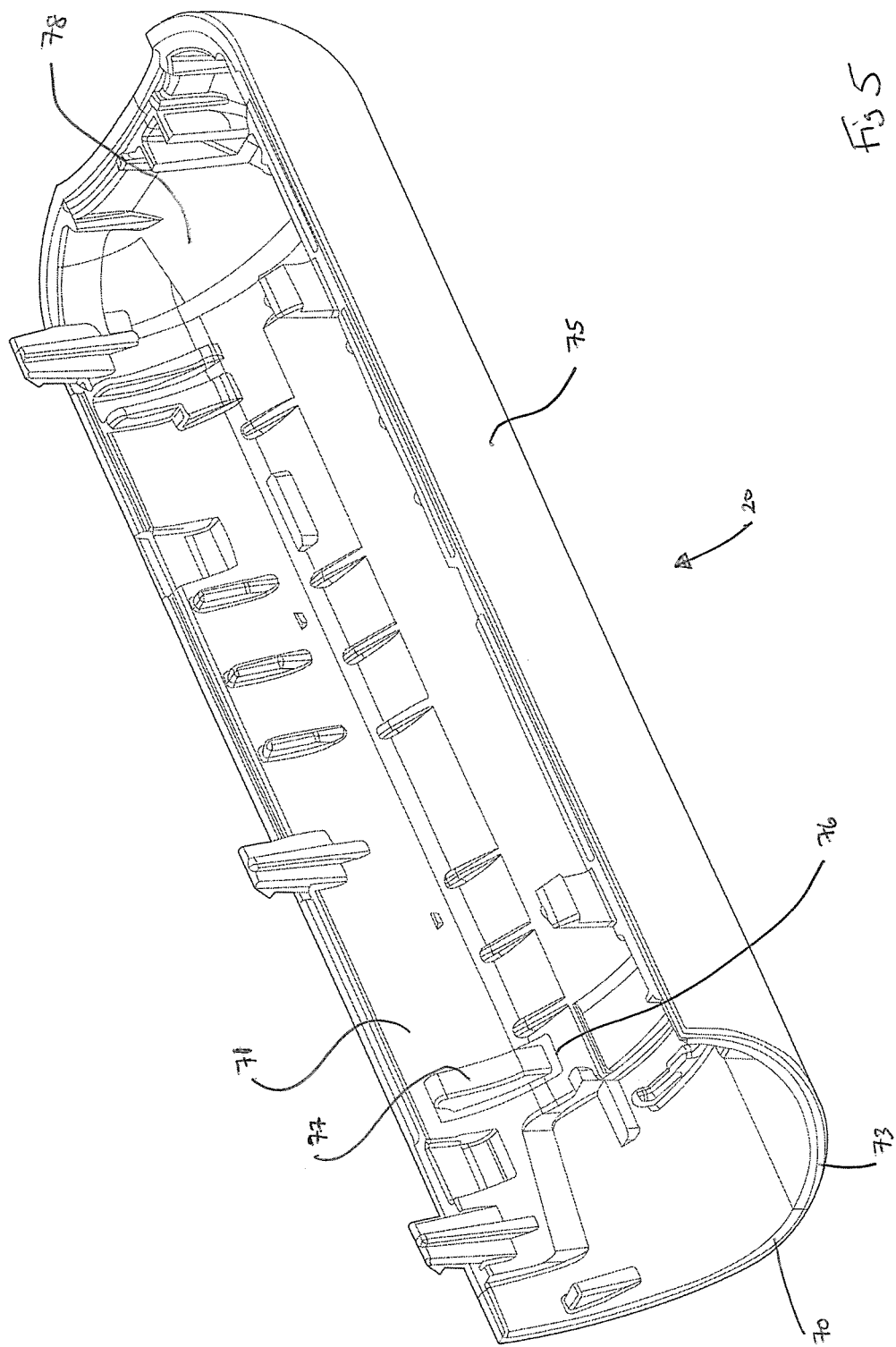

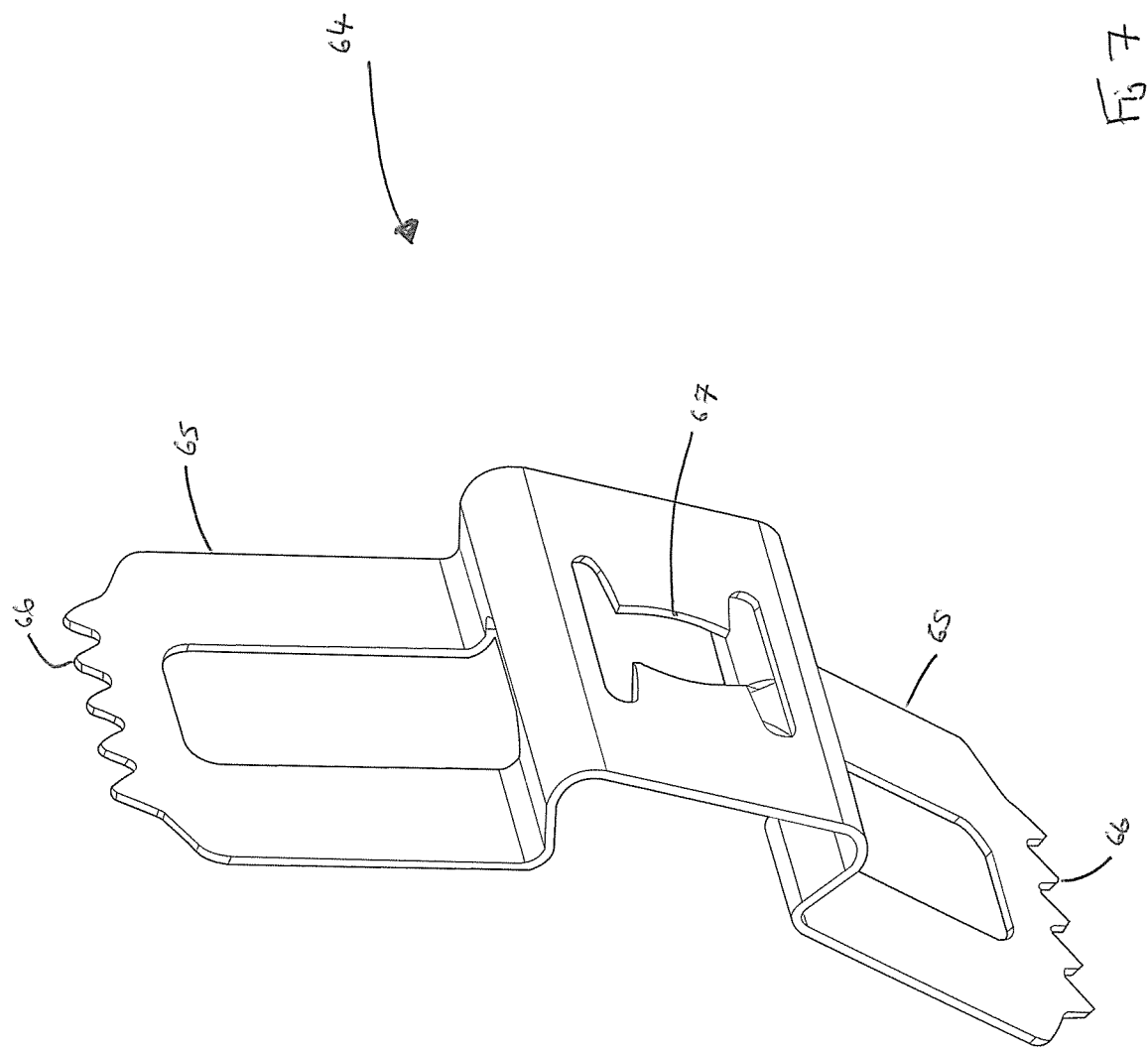

HOUSING PART FOR AN AUTO-INJECTOR

BACKGROUND

The present invention relates to a housing part for use in a housing for an auto-injector device for receipt of a syringe that is suitable for use in the injected delivery of a drug formulation to a patient.

It is well-known to use syringes for the delivery of injectable liquid drug formulation to a patient. Syringes rely on puncturing of the patient's skin by a hollow needle through which the injectable liquid drug (e.g. in solution or suspension form) is delivered to the muscle or tissue of the patient. Typically, syringes comprise a barrel for containing a volume of the liquid drug; a hollow needle defining a needle tip for dispensing of the liquid; and a plunger that is axially movable within the barrel.

It is also well-known to provide auto-injectors for use with syringes. Such auto-injectors typically comprise a housing comprising one or more housing parts for housing the syringe and an actuating mechanism, which is triggered in use, to allow for automatic delivery of the liquid drug formulation from the syringe. Actuating mechanisms typically comprise a source of drive (e.g. a strong spring) for drivable movement of a drive transfer element (e.g. a plunger rod) that transfers drive to the plunger for axial movement thereof within the syringe barrel. Such movement of the plunger results in the plunged driving of the liquid drug from the syringe barrel to the hollow needle for dispensing to the patient via the needle tip thereof.

For safety and hygiene reasons, it is desirable that the hollow needle does not protrude from the housing of the auto-injector other than when expelling the liquid drug formulation during an injection procedure. Thus, auto-injectors have been developed in which, the housing is arranged such that a needle receiving part allows for the needle of the syringe to be axially moveable therein from a first (i.e. rest) position in which the hollow needle is shrouded by the needle receiving part to a second (i.e. use) position in which at least the tip of the needle protrudes from that needle receiving part of the housing for penetrating the skin of the patient to an injection position. Only when the needle is at such injection position should it be possible for drug delivery to commence. Thus, auto-injectors have been developed which provide a two stage actuating mechanism, which first acts to transfer drive force to move the syringe from the 'rest' to the 'use' position, and which only then secondly acts to transfer drive force to the plunger for expelling of liquid drug contents from the syringe barrel.

The majority of auto-injectors are configured as a single device that incorporates both syringe and actuating mechanism in the same device housing. It is common for such devices to be arranged to be disposable such that following injected delivery of the liquid drug formulation, and typically also following retraction of the syringe back into the housing, the whole device may be safely disposed of.

SUMMARY

In general terms, the housing of the auto-injector functions to protect the elements of the auto-injector housed thereby. Desirably, the housing acts to protect these elements in the event of mechanical impact such as may arise when the auto-injector is dropped onto a hard surface. Particular aspects of the protective function include preventing any breakage of elements of the auto-injector including the syringe, which is typically comprised of glass; and/or preventing any undesirable displacement or movement of functional elements within the housing, particularly any unintended firing of the actuating mechanism.

Known auto-injector housings comprise a shell form formed of a relatively hard or generally incompressible material. In aspects, the shell may be comprised of one or more housing parts, for example having a clam-shell form. In other aspects, the front and rear housing may be comprised of front and rear housing parts that mate together to form the housing as a whole. It is also known to provide over-coating formed of a relatively softer or more compressible material to parts of the shell to provide a mechanical impact damping function or a soft-grip surface for holding by the hand of the user.

Applicant has now found that improved protective function in the event of mechanical impact may be provided where the housing of the auto-injector comprises one or more housing parts comprising a shell form body defining inner and outer shell surfaces and comprising a relatively hard or generally incompressible material; an over-coating formed of a relatively softer or more compressible material, the over-coating covering at least part of the outer shell surface of the shell form body; and at least one window defined in the shell form body, wherein the over-coating extends into the at least one window.

PCT patent publication no. WO2012/103,141 describes an automatic injection device comprising a housing enclosing a cavity for accommodating a container. A first over-moulded gripping surface extends longitudinally along a portion of the housing on a first exterior surface of the housing; and a second over-moulded gripping surface extends longitudinally along a portion of the housing on a second exterior surface of the housing opposite to the first exterior surface.

PCT patent publication no. WO2014/033,141 describes a medical device with a body that is flexibly deformable in response to mechanical impact above a predetermined threshold.

According to one aspect of the present invention there is provided a housing part for an auto-injector comprising a shell form body defining inner and outer shell surfaces and comprising a relatively hard or generally incompressible material;

an over-coating formed of a relatively softer or more compressible material, said over-coating covering at least part of said outer shell surface of said shell form body; and at least one window defined in the shell form body, wherein said over-coating extends into said at least one window.

These and other embodiments of the present invention are set forth in the later description, which describes for illustrative purposes only various embodiments thereof.

In relation to aspects of the auto-injector device described herein the term 'forward' is used to mean that end of the device, which locates closest to the injection site in use (i.e. the needle tip end) and the term 'rear' or 'rearward' is used to mean that end of the device, which locates furthest from the injection site in use. The term axial herein is used by reference to an axis, which runs from the forward end of the device to the rearward end of the device, and which typically corresponds to the axis of the syringe.

There is provided a housing part for use in a housing for an auto-injector device that is arranged for use with a syringe that contains a liquid drug formulation. The syringe is arranged to be suitable for use in the injected delivery of the liquid drug formulation to a patient. The housing comprises one or more housing parts for housing the syringe and an actuating mechanism, which is triggered in use, to allow for automatic delivery of the liquid drug formulation from the syringe.

The housing part comprises a shell form body, which defines an inner shell surface and an outer shell surface. The shell form body comprises a relatively hard or generally incompressible material. In embodiments, the shell form body comprises an acrylonitrile butadiene styrene material such as that sold under the trade name Lustran ABS 348 by Ineos AG of Avenue des Uttins 3, 1180 Rolle, Switzerland.

The housing part comprises an over-coating formed of a relatively softer or more compressible material. In embodiments, the over-coating comprises a thermoplastic elastomer material. In embodiments, the over-coating is comprised of a thermoplastic elastomer (TPE) material selected from the group consisting of styrene-ethylene/butylene-styrene (SEBS) block copolymers (such as those sold under the trade name Kraton) where the ethylene/butylene mid-block is a random copolymer which confers rubber like properties.

The hardness and resilience of the TPE can be determined by the relative proportion of the styrene and ethylene/butylene blocks and the addition of compounding agents such as mineral fillers and extender oils. Such TPE formulations are sold under the trade names Kraiburg, Mediprene and Versaflex. In embodiments the TPE material may alternatively be based on polymers from the groups Styrene-Ethylene/Propylene-Styrene (SEPS) block copolymers (e.g. Kraton, Septon), Styrene-Butadiene-Styrene (SBS), thermoplastic vulcanisates (TPV) incorporating vulcanised rubber inclusions (e.g. Santoprene). Similar considerations to the optimisation of properties apply as in the case of SEBS. In embodiments blends of the aforementioned polymers may also be utilised. In embodiments, the over-coating comprises a thermoplastic elastomer sold under the trade names GLS TPE OM1040 X-1 (Durometer Hardness 40 Shore A) or GLS TPE OM1060 X-1 (Durometer Hardness 60 Shore) by PolyOne Corporation of 833 Ridgeview Drive, McHenry, Ill. 60050 USA. In embodiments, the over-coating covers at least part of the outer shell surface of the shell form body.

In embodiments, the over-coating is comprised of a material that has a hardness of from 40 Shore A to 60 Shore A, such as from 40 to 50 Shore A, more particularly 42 Shore A. In embodiments, the optimum mix of impact absorbing performance, durability and tactile sensation is achieved by testing and laboratory experiment.

The housing part has at least one window (i.e. window opening or aperture) defined in the shell form body. The window extends from the inner to the outer shell surface of the shell form body.

The size and positioning of the window in the housing part may be determined by reference to the exact functional requirements of the housing part, particularly in relation to impact resistance. In embodiments, a first window is provided to the rear of the shell form body. In embodiments, a second window (e.g. of smaller size than the first window) is provided to the shell form body at a position forwards of the first window.

The over-coating extends into the at least one window (opening or aperture). In embodiments, the over-coating extends into the at least one window to at least the depth of the inner shell surface. In embodiments, such extending of the over-coating allows for creation of a bond (e.g. chemical) with the inner shell, enabling both parts to work as a hybrid deforming surface providing impact absorbing properties.

In embodiments, the over-coating extends into the window beyond the depth of the inner shell surface to define an inwardly protruding element. In embodiments, such extending of the over-coating allows for creation of a bond (e.g. chemical) with the inner shell and/or with an (e.g. neighbouring or compliant) inward protrusion of the inner shell, enabling the over-coating to have additional compressive capacity and/or providing greater impact absorbing properties.

In embodiments, the over-coating is provided as an over-moulding to the shell form body. In embodiments, the shell form body is formed by a first moulding process and the over-coating is provided by a second moulding process. In embodiments, the shell from body and over-coating have a co-moulded form.

In embodiments, the shell form body has a clam shell form. In embodiments, the shell form body has a cylindrical or ellipsoidal clam shell form and thus, two cylindrical or ellipsoidal clam shell form housing parts may be brought together to define a cylindrical or ellipsoidal housing form.

In embodiments, the housing part defines a rearward part of a housing for an auto-injector. In embodiments, the window is provided towards the rear end of the rearward housing part. In embodiments, the over-coating provides a gripping surface for gripping of the rearward part by a user.

In embodiments, the impact resistance of the housing part in response to dropped shock impact is determinable by reference to a standard drop test. For example, ISO 11608-1:2012 specifies a drop test involving 10 new devices dropped in a non-turbulent way in a horizontal orientation; 10 new devices dropped in a non-turbulent way in a vertical A orientation; and 10 new devices dropped in a non-turbulent way in a vertical B orientation, each drop being from a height of 1 metre onto smooth, hard, rigid steel of 3 mm thickness, backed by wood whose thickness is greater than 10 mm.

The housing part is suitable for use in a housing for an auto-injector. In embodiments, the housing comprises one or more housing parts, as described above.

There is also provided an auto-injector. The auto-injector comprises a housing as described above, which defines a housing cavity. The housing cavity is arranged for receipt of a syringe and is therefore typically sized and shaped for this purpose. The housing may be arranged as a single part or a multi-part (e.g. two part) housing assembly.

In embodiments, the syringe is movable within the housing such as in a direction parallel with or along the drive axis. In embodiments, the syringe is movable within the housing from a first position, in which the needle tip of the syringe is within the housing to a second position, in which at least the needle tip protrudes from a needle projection aperture thereof.

The syringe that is receivable within the housing cavity comprises a syringe barrel for holding a volume of a liquid drug formulation; a hollow needle at a front end of the barrel, the hollow needle defining a needle tip for dispensing of the liquid drug formulation; and a plunger (e.g. in the form of a rubber stopper) that is axially movable within the syringe barrel. The syringe plunger is movable axially within the barrel so as to enable the liquid drug formulation to be expelled from the barrel and thence through the hollow needle via the dispensing tip for injection into the patient. The syringe barrel is typically comprised of glass but may also be comprised of a relatively hard plastic polymer such as hardened polyethylene, polycarbonate or cyclic olefin polymers.

In embodiments, the plunger is comprised of a natural or synthetic polymer friction material, which frictionally interacts with the side wall of the syringe barrel. Suitable plunger materials include natural or synthetic rubbers or elastomeric materials.

In more detail, the syringe barrel is selected such as to define a barrel chamber for containing a suitable volume of the liquid drug formulation. In embodiments, that suitable volume is selected to correspond to a single dose of the drug formulation to be delivered to the patient. In other words, delivery of that single dose involves expelling the majority of the liquid drug formulation contents of the barrel chamber through the hollow needle for injection into the patient.

In embodiments, the rear end of the syringe barrel is provided with an end flange. In embodiments, the forward end of the syringe barrel is shaped to provide a shoulder. In embodiments, forward of that shoulder the syringe narrows further into a neck, which typically forms the needle-holding part thereof.

In embodiments, the needle barrel is provided with a syringe carrier that is arranged to fit over part or all of the length of the needle barrel. The syringe carrier may also extend out beyond the syringe barrel to wholly or partly enclose a length of the forward shoulder of the syringe barrel and of the hollow needle that extends from (the forward shoulder) of the syringe barrel.

In embodiments, the syringe carrier is arranged for receipt by the syringe barrel and fits at least partly over the flange of the rear end of the syringe barrel. In embodiments, the syringe carrier is arranged for snap fitting over the end flange of the syringe. In embodiments, the flange is effectively capped by the relevant 'end flange' part of the syringe carrier. In embodiments, a syringe flange guard element is provided to the syringe carrier.

In embodiments, the syringe carrier is provided with one or more slits in the wall(s) thereof such as to define flexible fingers, which allow the syringe carrier to flex open. In embodiments, the presence of such flexible fingers is of utility during assembly of the sleeved syringe as the needle cover (e.g. rigid needle shield), which typically has a larger diameter than the syringe barrel, passes through the centre of it when the syringe is pressed into the sleeve. In embodiments, the end flange at the rear end of the syringe then snaps into the rear end of the syringe carrier such that the syringe is locked into the sleeve once assembled.

In embodiments, one or more positioning and/or retaining features are provided to the housing for positioning and/or retaining the syringe and/or syringe carrier in the housing cavity. In embodiments, the one or more positioning and/or retaining features comprise one or more snap features provided interiorly to the housing.

In embodiments, the forward shoulder of the syringe is provided with one or more shoulder support features. In embodiments, the one or more shoulder support features are integral (e.g. integrally formed) with the housing. In other embodiments, the one or more shoulder support features are defined by one or more separate shoulder support parts provided to the housing.

The hollow needle defines a needle bore, which is most typically of circular cross-section and of selected bore diameter. It may be appreciated that in embodiments, the bore diameter may affect the force required to expel the liquid drug formulation through the needle and also the velocity at which the liquid drug formulation is expelled.

Examples of typical needles that are suitable for use therein include 12.5 mm ("half inch") long thin wall needles of grade 23 G, 25 G or 27 G. These have a needle bore of from about 0.2 to 0.4 mm such as from 0.24 to 0.37 mm. Other examples include both regular and thin wall needles used in conventional syringes including those with bevels such as 3 and 5 bevels.

The housing and any inner housing sub assembly thereof is shaped to define a housing cavity within which the syringe is receivable, and in embodiments, a needle projection aperture. The housing cavity is typically cylindrical in form, thereby matching the typically cylindrical outer profile of a syringe. The housing cavity may be further shaped with any manner of grooves, indentations or other shaping or surface details to define a 'lock and key' relationship between the housing and any inner housing sub assembly thereof and the syringe. Colour guides, arrows and any other surface markings may also be employed.

Typically, the housing and/or any inner housing sub assembly thereof is provided with a barrel receiving part for receiving the barrel of the syringe; a plunger receiving part for receiving the plunger of the syringe; and in embodiments, a needle receiving part for receiving the hollow needle of the syringe.

In embodiments, the plunger receiving part of the housing and/or any inner housing sub assembly thereof allows the plunger within the syringe barrel to be received thereby and for the plunger to be movable (e.g. axially) therein from a first position to a second position, in which it is moved somewhat into the syringe barrel. During use the plunger is in embodiments, movable to a fully plunged position at which, in most embodiments all of the liquid drug formulation contents of the barrel have been expelled.

In embodiments, the needle receiving part of the housing and/or any inner housing sub assembly thereof includes a needle projection aperture through which the hollow needle may protrude from the housing, for example during expelling of the liquid drug formulation through the hollow needle and its needle tip for delivery to the patient.

In embodiments, the syringe is movable within the housing cavity from a rest position, in which the needle tip is within the housing to a use position, in which the needle tip protrudes from the needle projection aperture.

Where the syringe is movable in the housing, it may be desirable for safety and hygiene reasons that the needle does not protrude from (i.e. out with) the housing other than when expelling the liquid drug formulation during an injection procedure. Thus, the housing and/or any inner housing sub assembly thereof and housing cavity defined thereby is generally arranged such that the needle receiving part thereof allows for the needle of the syringe to be axially moveable therein from a first position in which the needle is wholly housed (or shrouded) by the needle receiving part to a second position in which at least the tip of the needle protrudes from that needle receiving part of the housing.

In embodiments, where the syringe is movable within the housing, the housing includes biasing means (e.g. a return spring) arranged such that the needle is normally biased towards the first position, wherein such biasing means are overcome during the actuation of the syringe (e.g. by an actuating mechanism) to allow for movement of the needle to the second position.

In embodiments, the housing is provided with a removable cap that fits over and thereby, acts such as to close off, the needle projection aperture. It may therefore, be appreciated that when in the capped position, the removable cap acts such as to prevent ingress of contaminants into the needle receiving part of the housing.

In embodiments, the syringe further comprises a needle cover defining a needle sheath arranged in a sheathing configuration for sheathing (e.g. sealing) of the needle tip.

In embodiments, the needle sheath is comprised of a (e.g. resiliently) compressible material such as a natural or synthetic rubber material. In a storage configuration, the needle tip sticks into (e.g. is spiked or staked into) the needle sheath such that sealing of the needle tip is achieved. Usually, at least the first 3 to 4 mm of the needle tip end is so sheathed. It will be appreciated that for clinical reasons, the sealing of the needle tip acts in embodiments, such as to prevent passage of contaminant, bacterial or otherwise, through the needle tip and thus into the needle bore and syringe barrel chamber. Sterile sealing is preferred.

In embodiments, the needle cover is provided with a needle sheath cover for covering the needle sheath thereof. In embodiments, the needle sheath cover is comprised of a rigid material (e.g. polypropylene). In embodiments, the needle sheath cover is provided with one or more gripping elements (e.g. hooks) arranged for gripping of the needle sheath. In embodiments, the needle sheath is provided with one or more features arranged for receipt of the one or more gripping elements such as one or more indents, grooves or cavities.

In embodiments, the needle cover is provided to (e.g. fixed to or integral with) a removable cap for the housing. Thus, in embodiments, the needle cover projects within the cap such that when the removable cap is in the capped position the needle sheath and any needle sheath cover therefor is arranged for receipt of the needle tip of the syringe. In such embodiments, when in the capped position, the needle tip is sheathed by the needle sheath, and when the cap is removed the needle sheath and any needle sheath cover therefor are also removed such as to thereby, unsheathe the needle tip. In embodiments, the removable cap defines an essentially closed cylindrical cap chamber, optionally tapering, and the needle sheath and any needle sheath cover are provided along the axis of that cylindrical chamber.

In embodiments, the interior of the removable cap is provided with a connector defining one or more needle cover gripping elements for gripping the needle cover (i.e. gripping the needle sheath and/or any needle sheath cover therefor). In embodiments, such gripping elements are arranged for gripping the needle cover when in the capping position. In embodiments such gripping elements are (e.g. additionally) arranged for gripping the needle cover on removal of the cap such that removal of the cap also results in removal of the needle cover and hence, unsheathing of the needle tip. In embodiments, the needle cover gripping elements are arranged to project away from the top inner surface (e.g. of the cylindrical cap chamber) of the removable cap and towards its open end.

In embodiments, the connector comprises one or more needle cover gripping elements (e.g. gripping legs) attaching to a central hub. In embodiments, the connector is in the form of a cage-like needle cover gripper. In embodiments, each gripping element (e.g. leg) is provided (e.g. at the foot thereof) with one or more gripping protrusions such as one or more internally facing hooks or barbs. In embodiments, the internally facing hooks or barbs are disposed at an angle with respect to the gripping leg. In embodiments, the connector locates within the removable cap such that the central hub locates adjacent to or slightly spaced from the top inner cap wall or surface and the gripping legs project away from the top inner cap wall or surface and towards the open end of the cap. Other needle cover gripper arrangements are disclosed in PCT publication no. WO2009/081103, the entire contents of which are incorporated herein by reference.

In embodiments, the removable cap is provided with a connector. The connector is shaped to fit within and engage the needle cover and to engage the inner part of the removable cap. In embodiments, the connector includes one or more needle gripper elements in the form of first legs attaching to a central hub and spaced symmetrically away from one another, each first leg having one or more internally facing barbs pointing toward a forward region of the connector and adapted to engage a proximal region of the needle cover. In embodiments, the one or more internally facing barbs are disposed at an angle with respect to the first leg. In embodiments, the connector also includes one or more second legs spaced symmetrically away from one another, each second leg having one or more externally facing barbs located in the forward region of the connector and adapted to engage a forward region of the inner part of the removable cap or cap insert, as described below. In embodiments, the one or more first legs are biased initially at about 60 to 80 degrees with respect to the horizontal. Arrangements of removable cap and connector of this type are disclosed in PCT publication nos. WO2009/090499 and WO2010/007395, the entire contents of which are incorporated herein by reference.

In embodiments, particularly wherein the connector comprises one or more needle cover gripping elements (e.g. gripping legs) attaching to a central hub, it is desirable to position the connector within the removable cap such that the central hub is in spaced relationship to the top inner cap wall of the removable cap. When so-positioned, the gripping legs project away from the top inner cap wall and towards the open end of the cap.

In terms of function, the auto-injector is arranged to allow for actuation (i.e. firing) of the syringe. The auto-injector thus, also includes a drive transfer element for automatically transferring axial drive to the syringe. Preferably, that drive transfer element takes the form of a drive shuttle, but other suitable forms are also envisaged.

In preferred embodiments, the auto-injector includes an energy store for storing energy that can then be released to provide the axial drive to the syringe via the drive transfer element. In embodiments, the auto-injector includes a second coupling (e.g. in the form of a shuttle element) for coupling the energy store to the drive transfer element. In embodiments, the energy store comprises a mechanical energy store such as a spring (e.g. a compression or torsion spring). In other aspects, the energy store may be provided by a container of compressed liquid or gas propellant that on release provides a source of jet energy propulsion.

In embodiments, the energy store is able to exert an axial drive force of up to 60N on the syringe. Where the energy store is a compression spring the force exerted typically varies over the actuation profile such as from a range of 60 to 40N at the start of actuation to from 40 to 20N at the end of the actuation profile. Where the energy store is a compressed liquid or gas propellant a more constant force is typically exerted over the actuation profile.

In embodiments, release of axial drive force (e.g. actuation of the actuating mechanism) is responsive to a trigger (e.g. a user-actuable trigger). In embodiments, the trigger comprises a button, switch or lever arrangement. In other embodiments, a press actuation mechanism that is actuable in response to pressing of the housing of the device against the skin is envisaged.

In embodiments, the plunger end part of the drive transfer element is partly or wholly comprised of a natural or synthetic polymer friction material, which frictionally interacts with the side wall of the syringe barrel. Suitable plunger end materials include natural or synthetic polymers or elastomeric materials.

In embodiments, the auto-injector includes a first coupling for coupling the drive transfer element to the syringe barrel of the syringe. In embodiments, the drive transfer element is a plunger rod.

In embodiments, the first coupling is a reversible (e.g. demountable) coupling arranged for decoupling (e.g. demounting) when the syringe moves to the use position. In embodiments, the first coupling is at a forward position of the drive transfer element. Thus during a use operation, the first coupling is initially in place and axial drive force applied to the drive transfer element (e.g. drive shuttle) results in drivable movement of the syringe from the rest to the use position. That first coupling then decouples such that further axial drive force applied to the drive transfer element (e.g. drive shuttle) results in drivable movement of the syringe plunger within the syringe barrel, ultimately to a fully plunged position when most, preferably all of the liquid drug formulation contents of the syringe barrel have been drivably expelled therefrom.

In embodiments, the drive shuttle has an axially symmetric form such as cylindrical form, wherein the plunger rod for the syringe plunger (e.g. rubber stopper form) is suitably received axially within the cylindrical form. Guides (e.g. a central aperture of an end wall) may be provided to the shuttle to assist that axial receipt.

In embodiments, the shuttle is provided with one or more followers (e.g. pegs or notches) arranged for track-follower receipt by one or more tracks (e.g. grooves or slots) of the plunger rod, thereby coupling the movement of the plunger rod to that of the drive shuttle.

In embodiments, in a first actuation step the track-follower relationship is arranged such that on initial driven movement of the shuttle (and plunger rod) forward axial drive force is transferred to the plunger rod. In embodiments, in a further actuation step the track-follower relationship is arranged such that on subsequent driven movement of the shuttle (and plunger rod with sleeve) the driven shuttle and plunger rod become decoupled such that forward axial drive force is no longer transferred to the plunger rod. This corresponds to the fully plunged (or 'end of injection stroke') position of the device.

In embodiments, it is desirable for the auto-injector to allow for the needle of the syringe to be shrouded by a needle shroud element after use. Thus, in particular it is desirable to be able to provide a means of shrouding the needle of the syringe that is moved or otherwise brought into operation after completion of the injection procedure. Such means in embodiments, comprise a movable shroud element that is adapted to be movable to a shrouding configuration at the end of the injection procedure. Where the axial drive is provided by an energy store that couples to the drive transfer element by means of a second coupling (e.g. provided by reversible coupling of the drive shuttle to the plunger rod as described above) it has been appreciated that such movement of a needle shroud element ('needle shroud means') may be enabled if the movable needle shroud element couples (e.g. via a third coupling) to the source of axial drive, wherein said coupling is a reversible coupling arranged to be coupled when the plunger moves to a fully plunged position within the syringe barrel. Thus, at this fully plunged position, axial drive becomes transferable to the movable shroud element to move it into a shrouding position.

In another aspect, it is desirable for the auto-injector to allow for the needle of the syringe to be retracted into the housing after use, that is to say to retract the needle from the second (i.e. use) position to a retracted position that may in embodiments, correspond to the first (i.e. rest) position or in other embodiments, correspond to a third position, which in embodiments is further away from the needle delivery aperture. Where the axial drive is provided by an energy store that couples to the drive transfer element by means of a second coupling it has been appreciated that such syringe retraction is better enabled if the drive transfer element (e.g. plunger rod) reversibly couples to the energy store.

Thus, in embodiments, the energy store communicates with the drive transfer element via a second coupling, wherein the second coupling is a reversible coupling arranged for decoupling when the plunger end of the drive transfer element moves to a position that results in full plunging of the syringe plunger within the syringe barrel (e.g. provided by reversible coupling of the drive shuttle to the plunger rod and sleeve as described above). Thus, the second coupling is a reversible (e.g. demountable) coupling arranged for decoupling (e.g. demounting) when the syringe plunger has been moved to a fully plunged position. Ideally in use, once decoupled from the energy store (i.e. source of axial drive force) the drive transfer element is free to move such that reverse axial movement thereof is unhindered. A needle retract mechanism may then be arranged (e.g. responsive to a light return spring) to retract the syringe needle back into the housing unhindered by any interaction with the now free to move drive transfer element. Or alternatively, a needle shroud mechanism may be arranged to be activated at this point.

In embodiments, the auto-injector additionally comprises a second coupling for coupling the drive transfer element to a source of axial drive, wherein said second coupling is a reversible coupling arranged for decoupling when the syringe plunger moves to a fully plunged position within the syringe barrel.

In embodiments, the auto-injector additionally comprises a movable needle shroud element; and a third coupling for coupling the movable shroud element to said source of axial drive, wherein said third coupling is a reversible coupling arranged for coupling when the syringe plunger moves to a fully plunged position within the syringe barrel.

In embodiments, any or all of the first, second and third couplings are comprised within a common coupling element.

In embodiments, a reset mechanism is provided for resetting the firing mechanism after actuation thereof. The reset mechanism may for example, comprise a spring, motor, mechanical arrangement or a reset coupling.

Representative auto-injectors that may be modified in accord with the present invention include those described in U.S. Pat. Nos. 4,553,962; 4,378,015; U.S. 5,304,128 and PCT patent publication nos. WO99/22790 (Elan Corporation); WO00/09186 (Mediject Corporation); and WO2005/070,481 and WO2007/083,115 (The Medical House PLC) and PCT patent publications nos. WO2009/081,103, WO2009/081,130, WO2009/081,132, WO2009/081,133 and WO2010/007,395 (UCB Pharma SA), all of which are incorporated herein by reference.

In embodiments, the auto-injector is provided with child-resistant features to prevent undesirable actuation of the actuating mechanism by a young child.

According to a further aspect of the present invention there is provided a kit of parts comprising an auto-injector as described above but absent the syringe; and a syringe containing a liquid drug formulation.

According to a further aspect of the present invention there is provided a kit of parts comprising an auto-injector as described above but absent the syringe; and packaging therefor; and optionally a syringe containing a liquid drug formulation.

Suitable packaging typically comprises a container for the auto-injector and syringe. In embodiments, the packaging comprises a compartment for the auto-injector pre-loaded with the syringe. In embodiments, the packaging comprises a separate compartment for a 'kit' of the auto-injector and the syringe.

BRIEF DESCRIPTION OF THE DRAWINGS

The disclosure is further described with reference to the accompanying drawings, in which:

FIG. 3b is an exploded view of the rearward assembly parts of auto-injector of FIG. 1;

FIG. 4 is a perspective view of the clam shell body of the clam shell housing part of the rearward part of the auto-injector of FIG. 1, absent its over-coating;

FIG. 5 is a perspective view of the clam shell housing part of the rearward part of the auto-injector of FIG. 1 comprising the clam shell body of FIG. 4 and over-coating;

FIG. 7 is a perspective view of a latch spring part for use with the auto-injector of FIG. 1;

DETAILED DESCRIPTION

To provide an overall understanding of the systems, devices and methods described herein, certain illustrative embodiments will now be described. For the purpose of clarity and illustration these systems and methods will be described with respect to auto-injectors that are arranged to receive a syringe. It will be understood by one of ordinary skill in the art that the systems, devices and methods described herein may be adapted and modified as is appropriate, and that these systems, devices and methods may be employed in other suitable applications, and that other such additions and modifications will not depart from the scope hereof.

Figure 1:
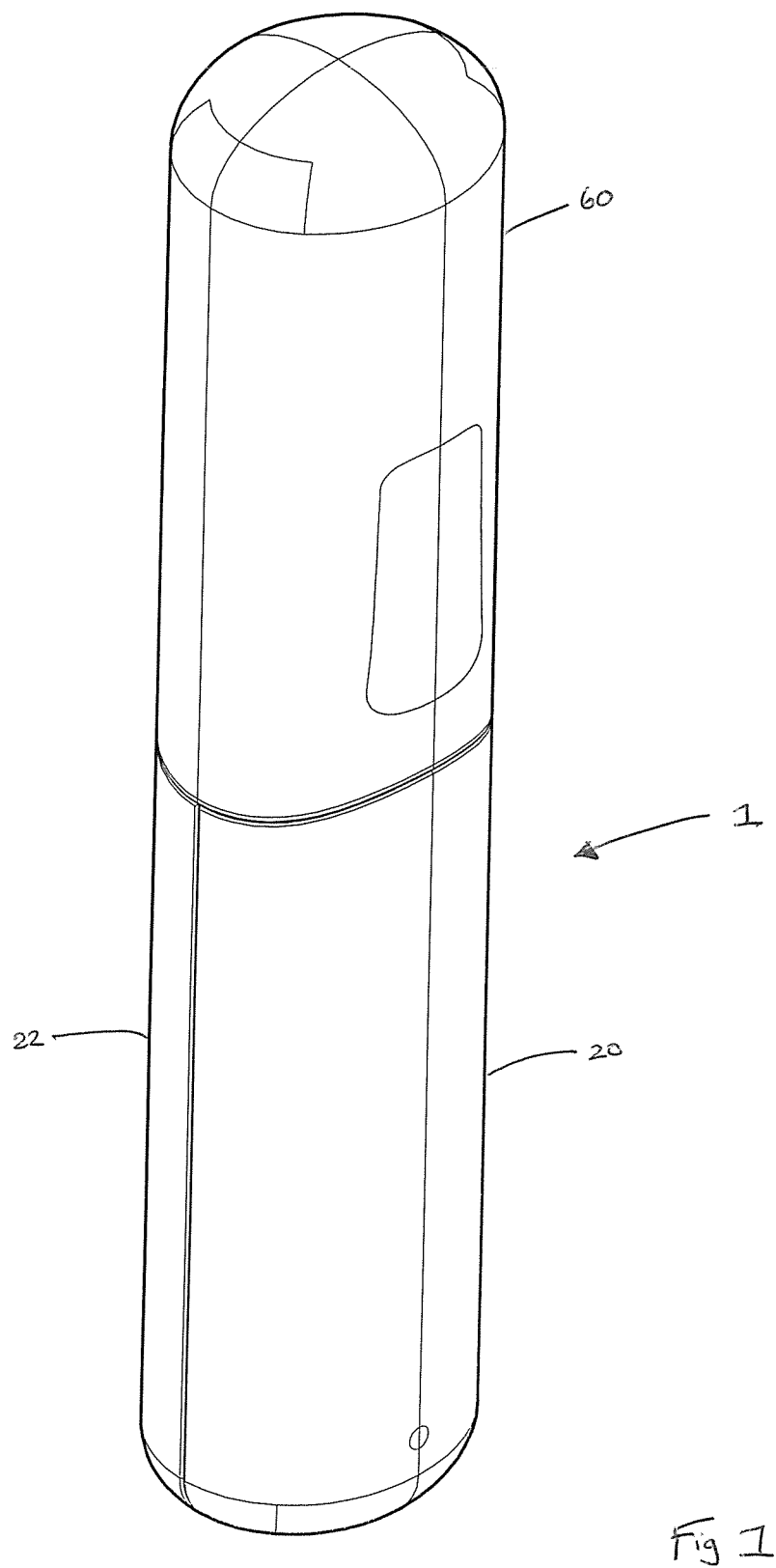
FIG. 1 is a perspective view of an auto-injector herein in the 'at rest' position with removable cap thereof in docked receipt by the outer housing thereof.
Figure 2:
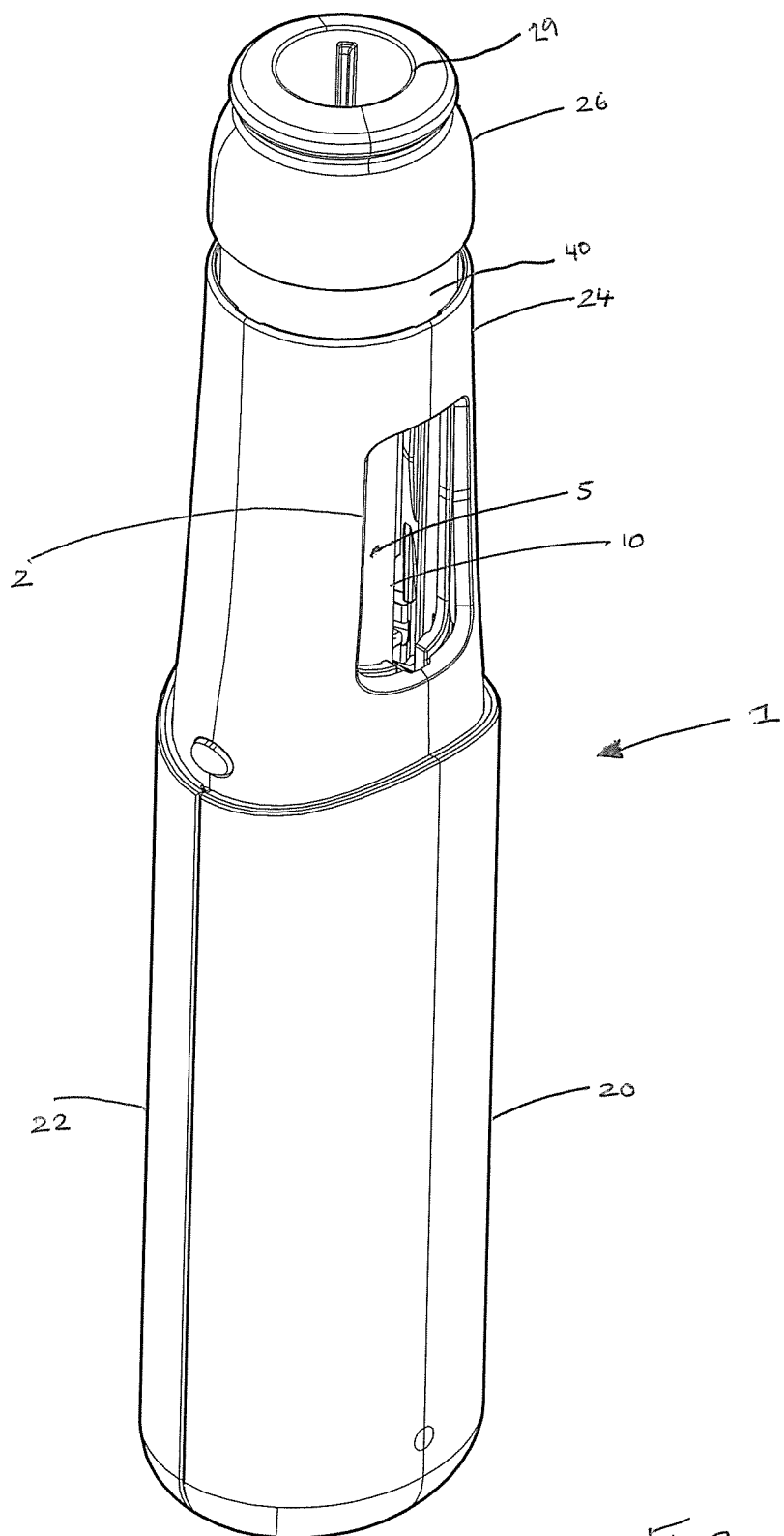
FIG. 2 is a perspective view of the auto-injector of FIG. 1 in the 'at rest' position with removable cap thereof removed from the outer housing thereof.
Figure 3A:
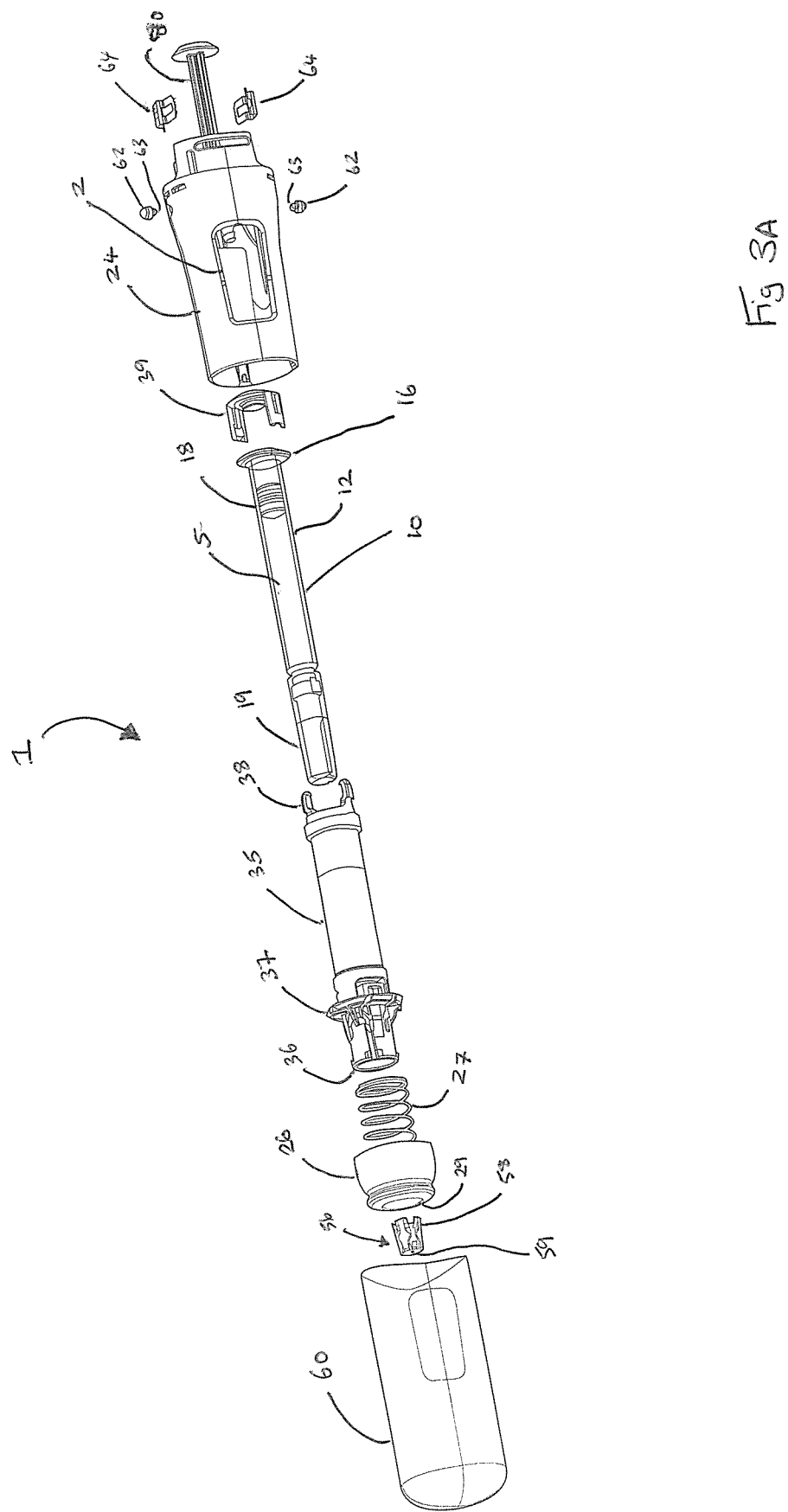
FIG. 3a is an exploded view of the forward assembly parts of auto-injector of FIG. 1.

Referring now to the drawings, FIGS. 1 and 2 show a first auto-injector device 1 herein, wherein FIG. 1 shows the device 1 in a capped configuration and FIG. 2 shows the auto-injector device 1 with its removable cap 60 removed. FIGS. 3A and 3B, in combination, show an exploded view of the auto-injector device 1, which is arranged for use with a syringe 10 that contains a liquid drug formulation 5. The auto-injector device 1 comprises a generally cylindrical form rear outer housing that is formed of two clam shell parts 20, 22; and a forward housing part 24, also of generally cylindrical form. The housing 20, 22, 24 is arranged for receipt of the syringe 10 and is sized and shaped for this purpose. The forward outer housing 24 is provided with a viewing port 2 that allows for viewing of the contents of the syringe 10 to check for dispensing of drug 5 there from.

The syringe 10 comprises a barrel 12 for holding the liquid drug formulation 5; a hollow needle 14 (not visible in FIGS. 3A and 3B, but see for example, FIGS. 8C and 9C) at a forward end of the barrel 12; a syringe flange 16 at the rear end of the barrel; and a syringe plunger 18 in the form of a rubber stopper that is arranged for axial movement within the barrel 12 in response to driven movement of plunger rod 80 such as to enable the liquid drug formulation 5 to be expelled through the hollow needle 14. The hollow needle 14 defines a needle bore, which is of circular cross-section (e.g. 23 G, 25 G or 27 G bore diameter) and a needle tip 15. The syringe 10 is further provided with a needle cover 17 (not visible in FIGS. 3A and 3B, but see for example, FIGS. 8A and 9A) and rigid needle shield 19.

The syringe 10 is received within syringe carrier 35, which has a forward lip 36 defining a forward opening; forward flange 37; and at the rear thereof is provided with pair of diametrically oppositely located trailing latch arms 38 arranged for receipt of syringe flange guard 39. In injected use (see for examples, FIGS. 8C and 9C), the tip 15 of the needle 14 of the syringe 10 protrudes from the opening defined by the forward lip 36 of the syringe carrier 35. The syringe 10 has limited axial movement within the syringe carrier 35, wherein interaction of the syringe flange guard 39 with the syringe flange 16 limits the extent of rearward axial movement thereof. As will be explained in more detail later, during injected use, drive force to move the syringe carrier 35 and syringe 10 carried thereby from a rest to an injection position is received by the syringe flange guard 39. Further details of a suitable syringe flange guard 39 for use herein are provided at Applicant's PCT publication no. WO2015/015,230.

Return spring 27 fits around the forward part of the syringe carrier 35 such that its rearward end abuts the forward flange 37 thereof. The forward end of the return spring 27 is received within forward head part 26 of the device 1, which forward head part 26 defines a needle delivery aperture 29.

Needle cover gripper 56 in the form of a cage-like (or 'flower') structure and defining plural gripping elements 58 arranged about a central hub 59 is further provided to the removable cap 60. Such gripping elements 58 are arranged for gripping of the rigid needle sheath shield 19 on removal of the removable cap 60 such that removal of the cap 60 also results in removal of the rigid needle sheath shield 19 and needle sheath 17 enclosed thereby, and hence, unsheathing of the needle tip 15.

As shown in FIG. 3B, the housing 20, 22, 24 of the auto-injector device 1 is arranged to receive an inner housing sleeve 40 that fixes by means of visual plug 42 to the rear housing part 20, 22 and that defines a threaded forward end 43 for threaded engagement with forward head part 26. The inner housing sleeve 40 defines an inner housing cavity within which the syringe 10 and its syringe carrier 35 are received. The inner housing sleeve 40 also defines a housing for drive spring 48; drive spring cap 49; and drive shuttle 50 having forward 52 and rearward legs 54, the action of all of which will be described in more detail hereinafter. Rear cylinder 45 fits around the rear end of the inner housing sleeve 40.

Figure 9A:
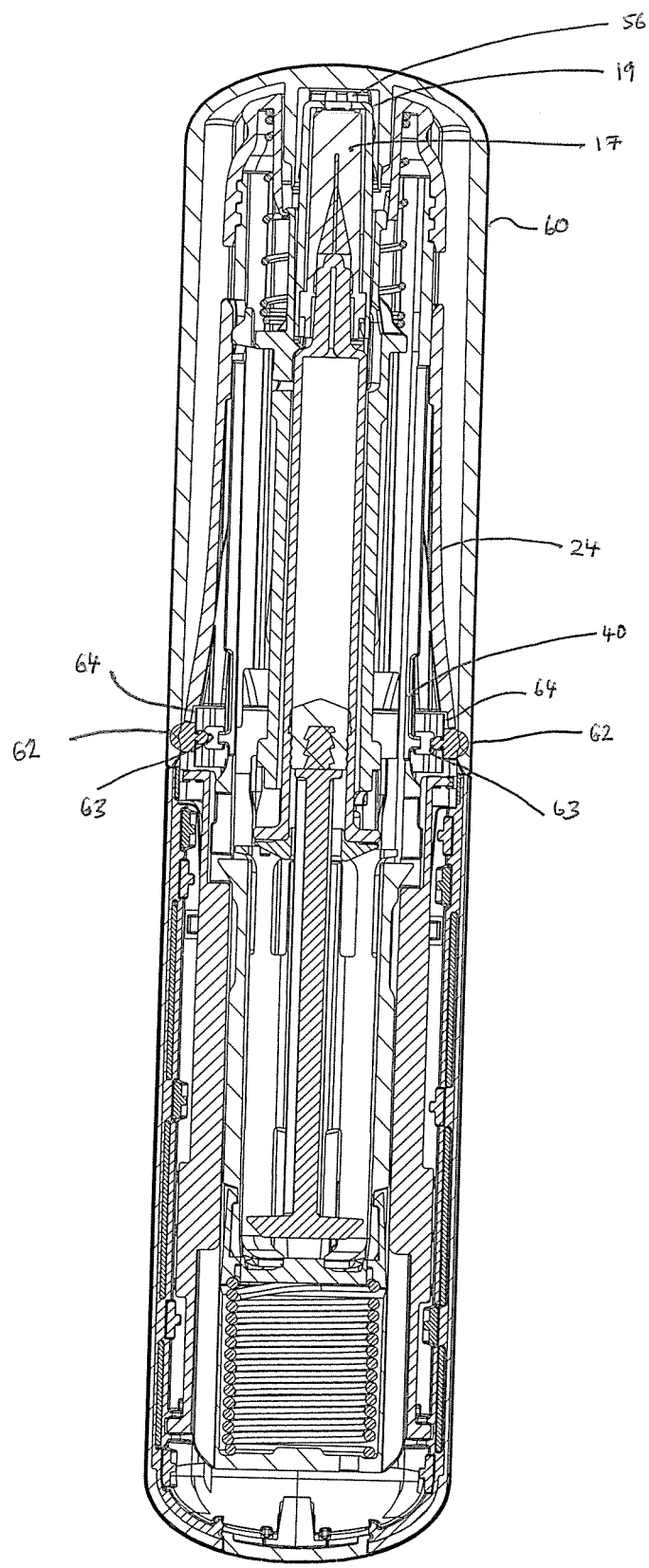
FIGS. 9A to 9E show second sectional views, which are rotated by 90° compared to the first sectional views of FIGS. 8A to 8E, of the auto-injector of FIG. 1 during sequential use steps thereof.

As shown in FIGS. 3A and 9A, the device 1 is provided with an anti-fire latch mechanism comprising a pair of buttons 62, each with inner head pip 63, that are received by apertures within forward housing part 24. Each button 62 co-operates with a latch spring 64, the form of which is shown in more detail in FIG. 7. The head pip 63 of each button 62 protrudes through pip-receiving aperture of the latch spring 64. Arms 65 with serrated edges 66 of each latch spring 64 seat within a latch spring 64 receiving cavity defined within the inner wall of the forward housing part 24. In the capped configuration of FIGS. 1 and 9A, the inner wall of the removable cap 60 acts to push in each button 62 against the bias of the latch spring 64 such that the radially innermost aspect of latch spring 64 interferes with the inner housing sleeve 40 such as to lock any relative movement of the inner housing sleeve 40 relative to the front housing part, thereby preventing any inadvertent actuation of the device 1. In the uncapped configuration of FIGS. 2 and 9B, the removable cap 60 has been removed, and thus can no longer act on the buttons 62. Under the biasing action of its latch spring 64, each button 62 is now pushed radially outwards such that the radially innermost aspect of latch spring 64 no longer interferes with the inner housing sleeve 40, thereby no longer locking any relative movement of the inner housing sleeve 40 relative to the front housing part. The uncapped device 1 may therefore now be actuated by user action, as will be described in more detail later.

Each of the two corresponding clam shell parts 20, 22 of the rear outer housing has an over-coated form, as will now be described in more detail by reference to FIGS. 4 to 6, which shows the detailed form of just one of these corresponding parts 20, 22.

FIG. 4 shows the cylindrical/ellipsoidal clam shell form body 70 of a clam shell housing part 20 of the rear outer housing of the device 1, which shell form body 70 defines inner 71 and outer 73 shell surfaces and comprises a relatively hard or generally incompressible material. A rear window 72 and a forward window 76 are defined in the shell form body 70. Rear housing 20, 22 is also shaped for receipt of visual plug 42 (see FIG. 3B).

FIG. 5 shows the clam shell form body 70 of FIG. 4, but now provided with an over-coating 75 formed of a relatively softer or more compressible material, and which over-coating 75 covers the outer shell surface 73 of the shell form body 70. The over-coating 75 is provided as an over-moulding to the shell form body 70. The over-coating 75 extends into the windows 72, 76 of the shell form body 72. The over-coating 75 extends into the rear window 72 to define a first window covering 78 that is of at least the depth of the inner shell surface 71. The over-coating extends into front window 76 beyond the depth of the inner shell surface 71 to define an inwardly protruding element 77.

Figure 6:
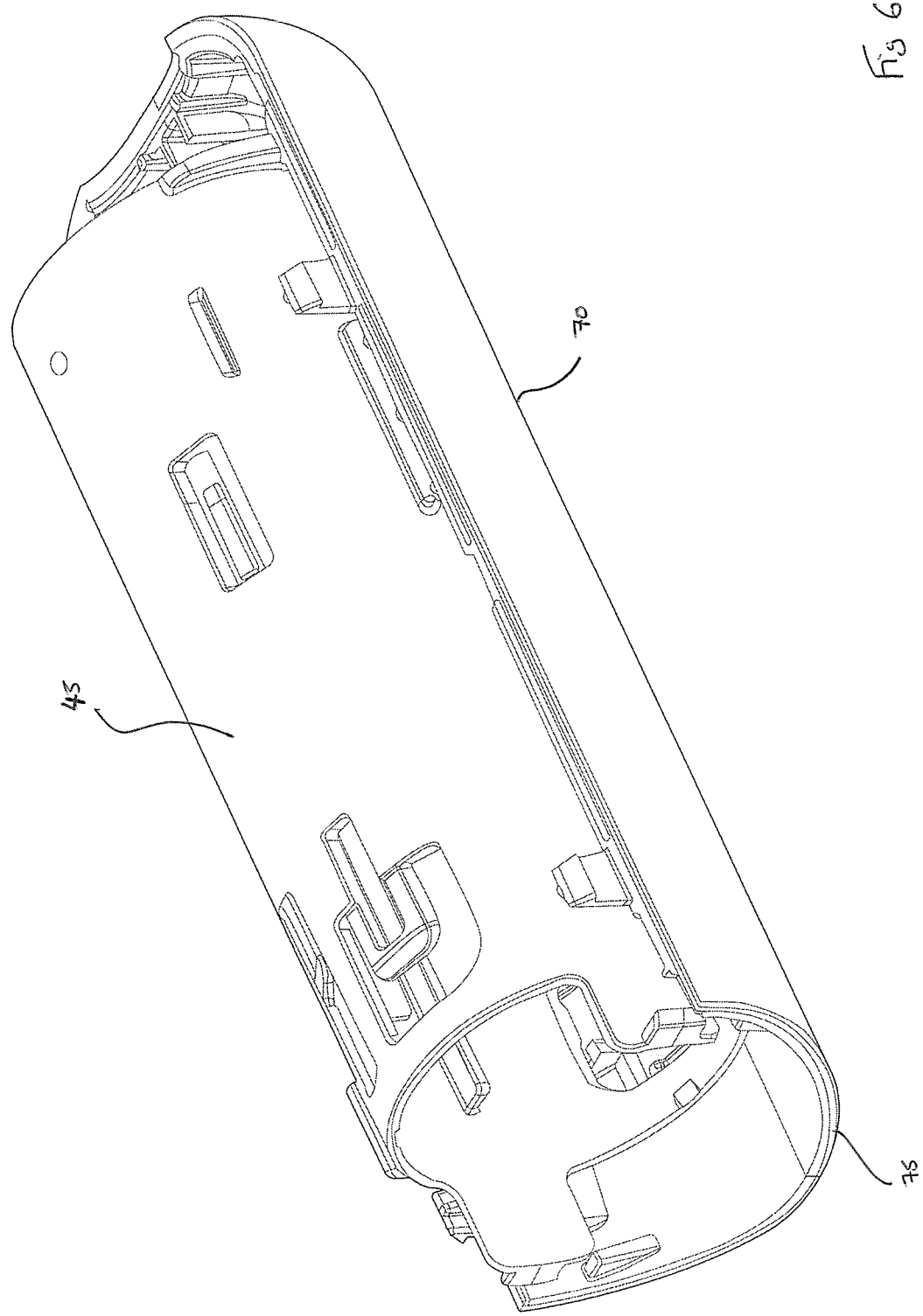
FIG. 6 is a perspective view of the clam shell housing part of FIG. 5 with rear cylinder element locating therein.

FIG. 6 shows the clam shell body 70 of FIG. 5 with its over-coating 75 and shows how the rear cylinder 45 locates therein.

The geometry and relative sizes of the windows 72, 76 are selected to optimise how the shell form body 70 with over-coating 75 deforms on impact and absorbs the energy of impact without falling apart or undesirably transmitting that energy elsewhere in the device 1. It was found that if the overall assembly is too stiff, then the energy of impact is not sufficiently absorbed. Alternatively if it is too pliable then it does not provide sufficient structural integrity. Suitable choices of materials for the shell form body and over-coating are defined hereinbefore. In embodiments, the shell form body comprises an acrylonitrile butadiene styrene material and the over-coating comprises a thermoplastic elastomer material.

Further aspects of the auto-injector device 1 herein may now be appreciated by reference to FIGS. 8A to 8E; and FIGS. 9A to 9E and to the following description of a typical use operation. For clarity, only the parts of FIGS. 8A to 8E; and FIGS. 9A to 9E most relevant to the use operation being described are labelled.

Figure 8A:
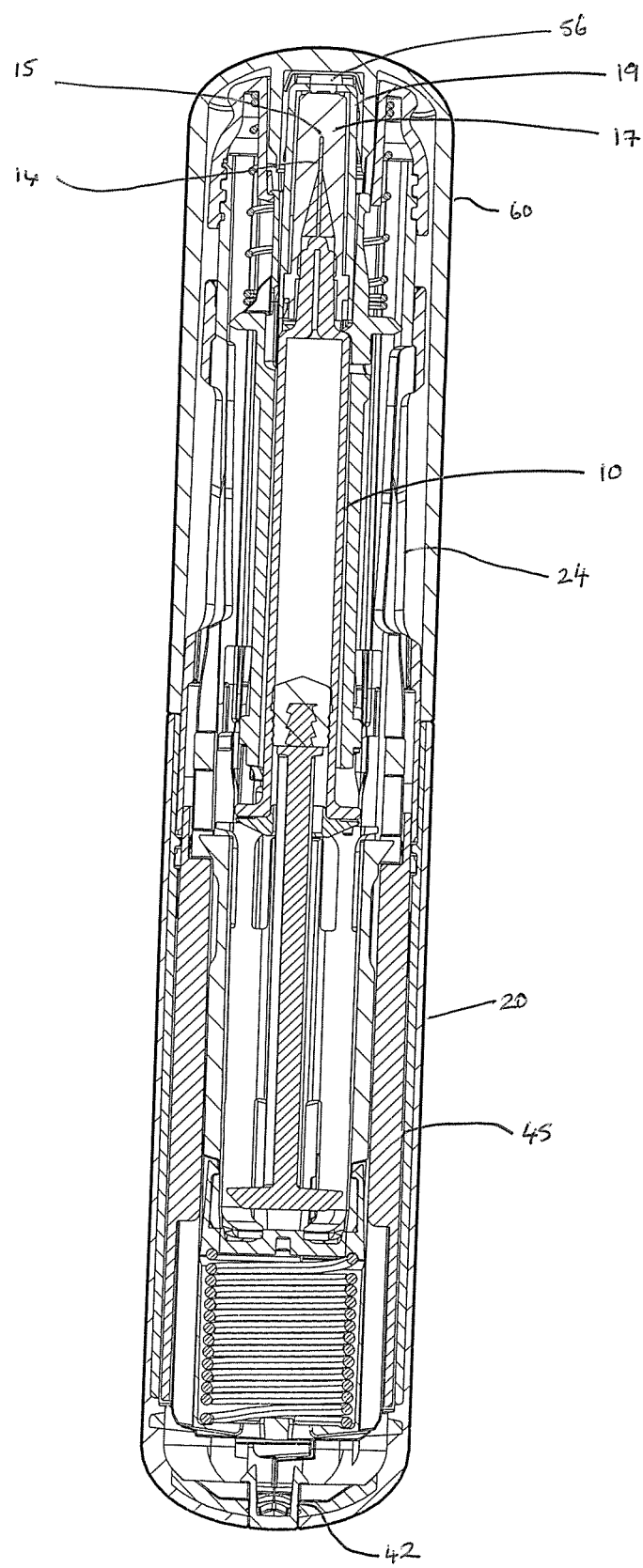
FIGS. 8A to 8E show first sectional views of the auto-injector of FIG. 1 during sequential use steps thereof.

In a first stage of a typical use operation, as shown at FIGS. 1, 8A and 9A the device 1 is 'at rest' and the removable cap 60 is in place. In this position, the needle 14 and dispensing tip 15 of the syringe 10 are sheathed by the needle cover 17 and its rigid needle shield 19. As best seen in FIG. 9A, the anti-fire latch mechanism 62, 64 acts to prevent any inadvertent actuation of the device 1, wherein the inner wall of the removable cap 60 acts to push in each button 62 against the bias of the latch spring 64 such that the radially innermost aspect of latch spring 64 interferes with the inner housing sleeve 40 to lock any unintended relative movement of the inner housing sleeve 40 relative to the front housing part 24.

Figure 8B:
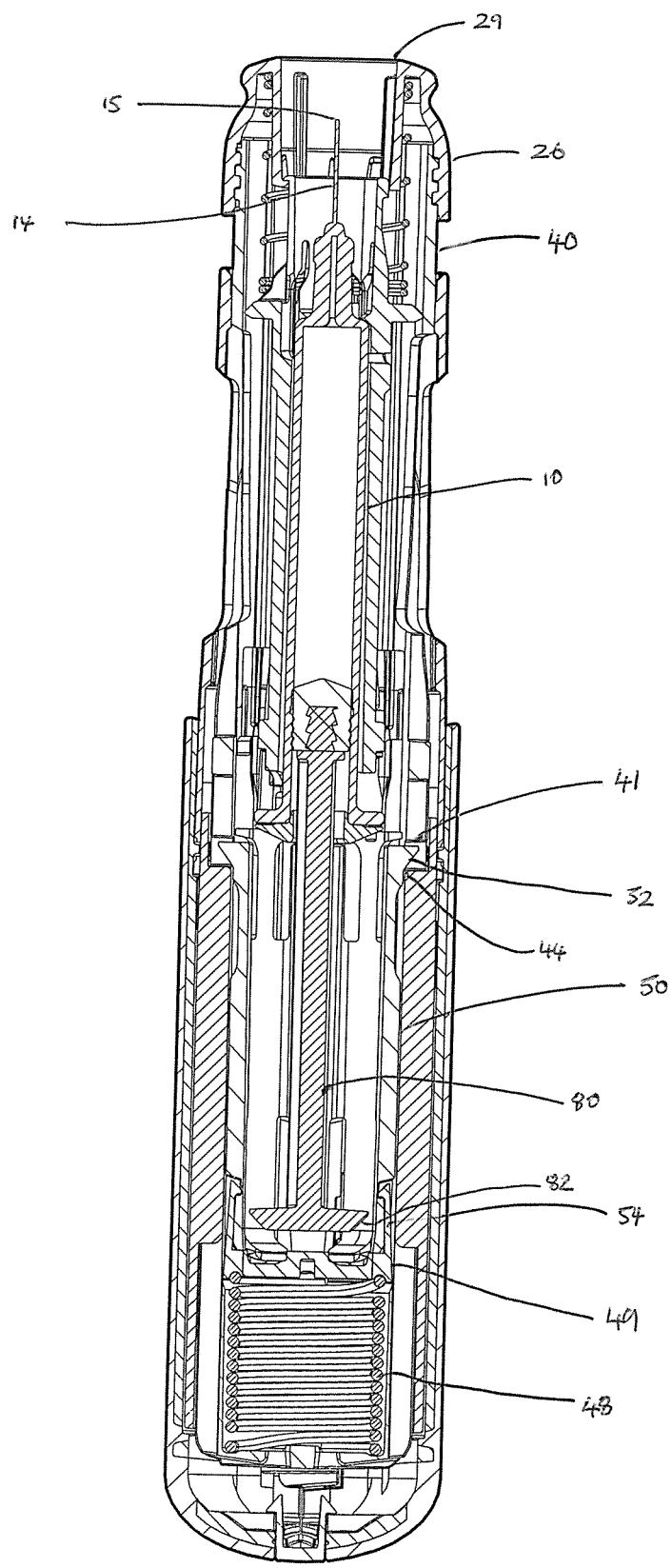
Figure 9B:
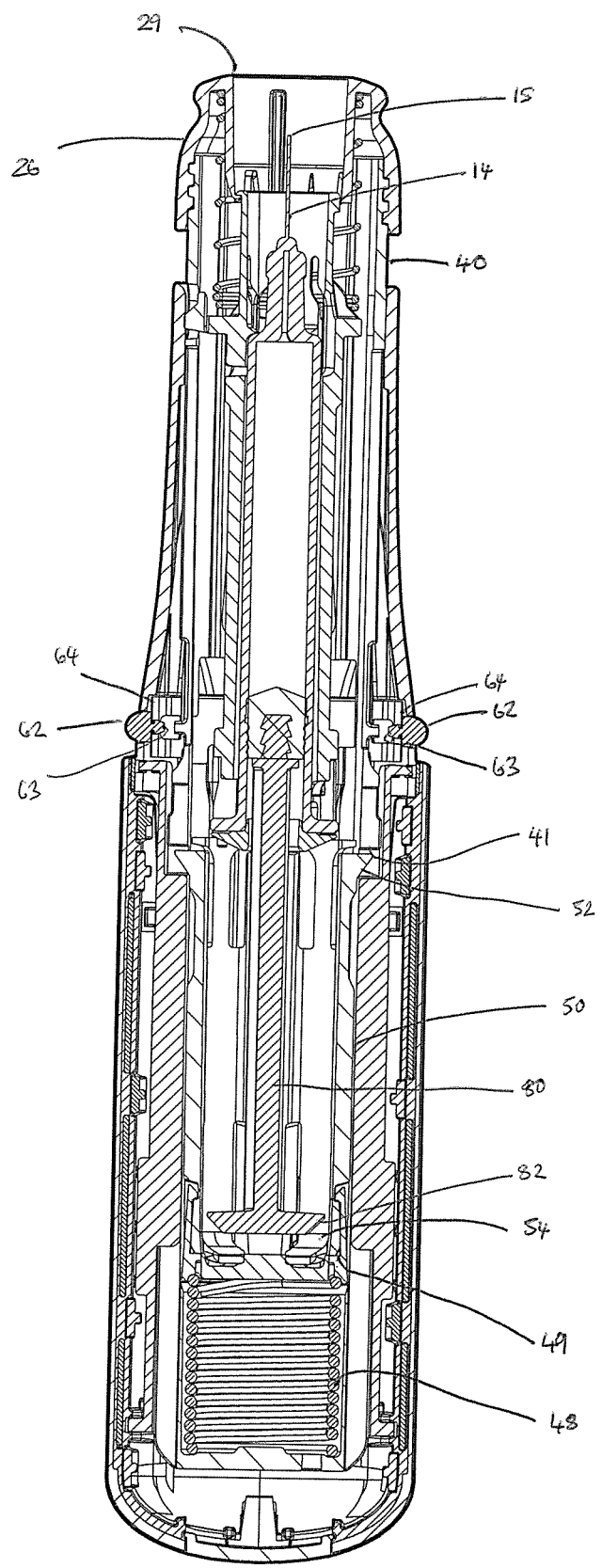

In a second stage of a typical use operation, as shown in FIGS. 2, 8B and 9B, the cap 60 has been removed to uncover the forward head part 26 of the device 1 and its needle delivery aperture 29. Removal of the cap 60 also results in removal of the rigid needle sheath shield 19 and needle sheath 17, which attach to the cap 60 by means of the needle cover gripper 56, and hence, in unsheathing of the tip 15 of the syringe needle 14.

The device 1 is now in its 'ready to use' state, in which it is noted that the tip 15 of the needle 14 remains surrounded by the forward head part 26. In this uncapped configuration, the removable cap 60 can no longer act on the buttons 62. Under the biasing action of its latch spring 64, each button 62 is now pushed radially outwards such that the radially innermost aspect of latch spring 64 no longer interferes with the inner housing sleeve 40, thereby no longer locking any relative movement of the inner housing sleeve 40 relative to the front housing part. The uncapped device 1 may therefore now be actuated in response to user action.

The user now grips the device 1 at the rear housing 20, 22 and places the needle delivery aperture 29 against the skin at the desired injection point. Pressure is now applied to the forward head part 26 by pushing this against the injection surface of the skin, which pressure results in rearward motion of the forward head part 26 and inner housing sleeve 40 relative to the housing 20, 22, 24. As a result of this motion, firing of the device 1 is actuated.

On actuation, the drive shuttle 50 is also initially moved slightly rearwards as a result of the engagement of the forward legs 52 thereof with a first ledge 41 of the inner housing sleeve 40. As the drive shuttle 50 moves forward, the rear legs 54 thereof are flexed inwards as a result of interaction with ribs (not visible) on the rear cylinder 45 to decouple from the inner housing sleeve 40. As a result of this inwards flexing, the rear legs 54 thereby form a 'hammer head', which can interact in driving fashion with the tapered drive head 82 of the plunger rod 80 to thereby couple the drive shuttle 50 and plunger rod 80.

The forward legs 52 define a ramped surface, which interacts with a second ledge 44 of the rear cylinder 45, the effect being to push the forward legs 52 inwards, thereby allowing for forward movement of the drive shuttle 50 relative to the inner housing sleeve 40 under the driving force of the drive spring 48 transferred via the drive spring cap 49. A further result of this inwards-flexing of the forward legs 52 is to bring the leading faces of the forward legs 52 into engagement with the rear face of the syringe flange guard 39 of the syringe carrier 35 assembly such that forward movement of the drive shuttle 50 also results in forward movement of the syringe carrier 35 and syringe 10 carried thereby.

Figure 8C:
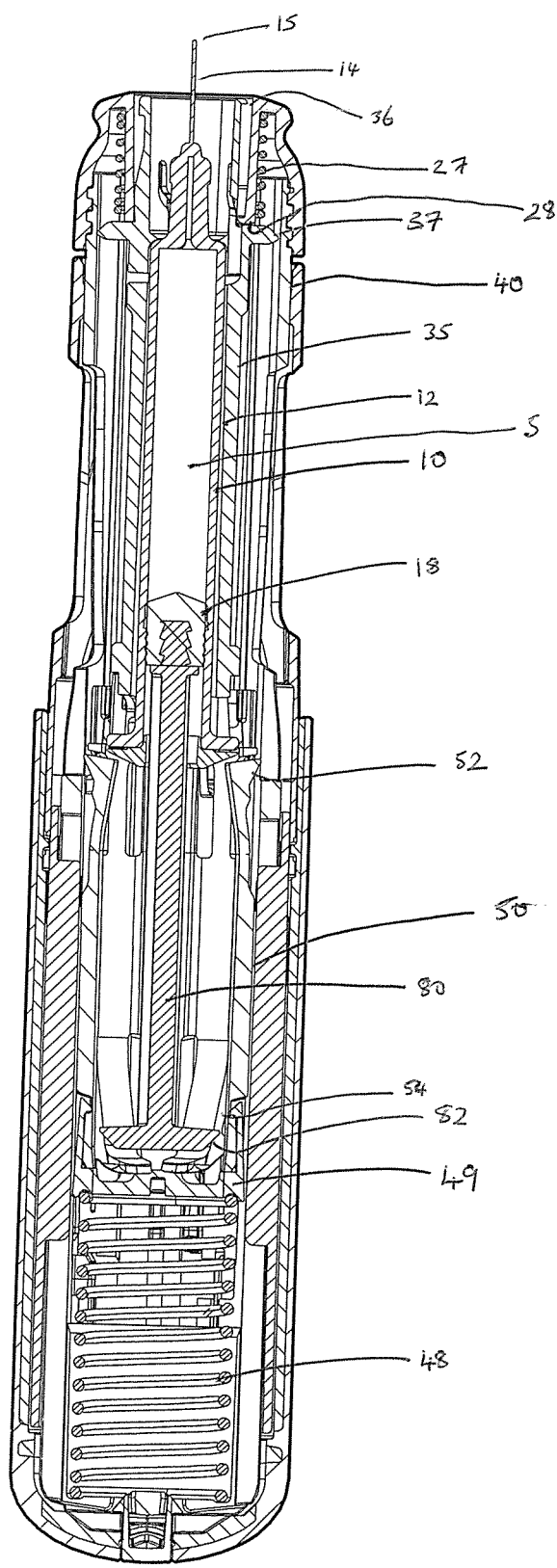
Figure 9C:
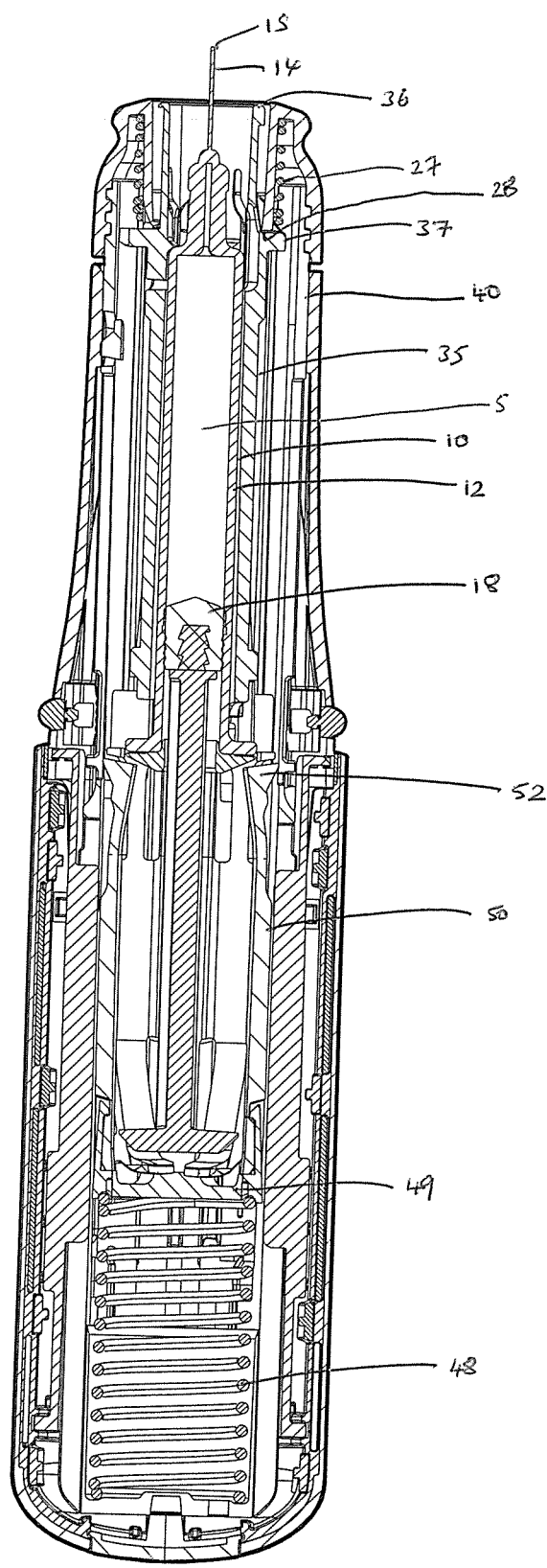

The drive shuttle 50 now moves forward under the drive force of the drive spring 48, thereby advancing the syringe carrier 35 and syringe 10 carried thereby to the 'syringe advanced' position of FIGS. 8C and 9C, in which the syringe needle tip 15 protrudes from the needle delivery aperture 29. Since the syringe stopper 18 does not move forward within the syringe barrel 12, no fluid 5 is expelled during this syringe advancement step. The advancement of the syringe 10 is only lightly resisted by the light return spring 27, which interacts with the forward end flange 37 of the syringe carrier 35. At the 'syringe advanced' position the forward flange 37 of syringe carrier 35 abuts a projecting circular inner end wall 28 of the front housing part 26 and further forward movement of the syringe 10 is prevented.

At or about this point, the forward legs 52 of the drive shuttle flex outwardly into the front slot 44 (see FIG. 3B) of the inner housing sleeve 40 such as to enable disengagement of those legs 52 from the syringe flange guard 39 of the syringe carrier 35, thereby decoupling the drive shuttle 50 from the syringe carrier 35 and syringe 10 carried thereby.

Figure 8D:
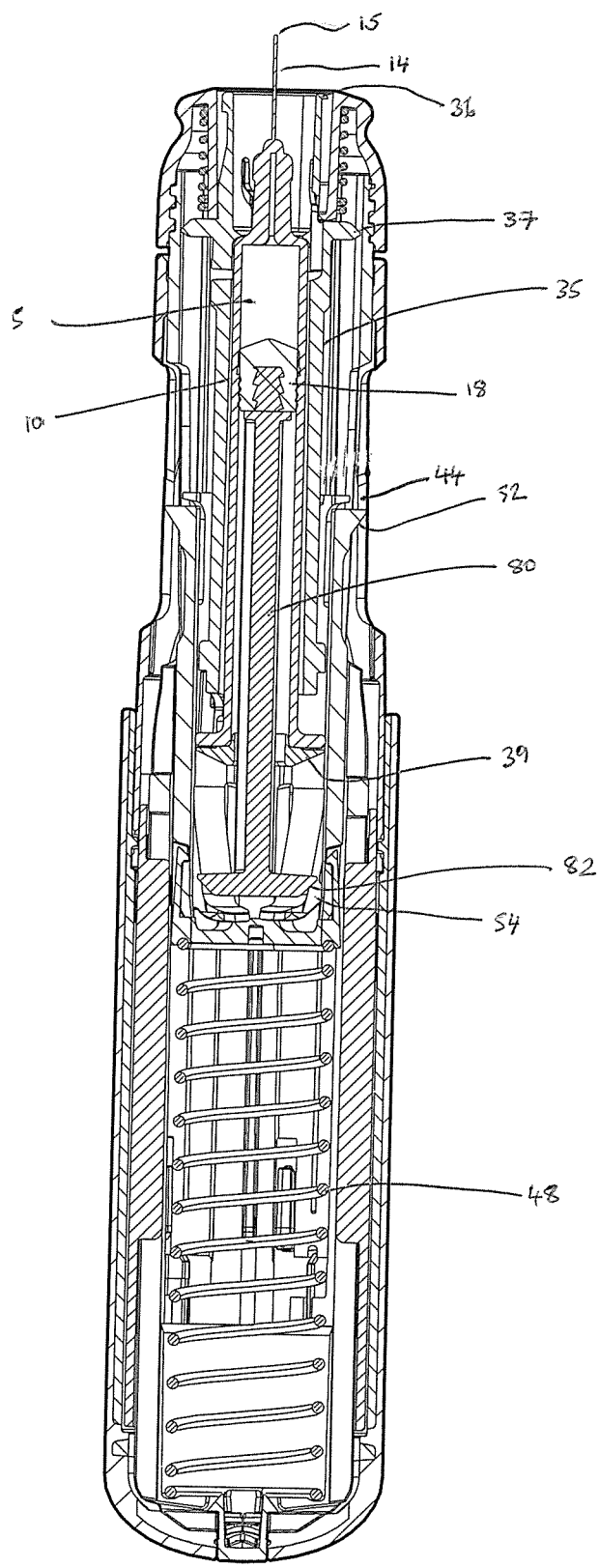
Figure 9D:
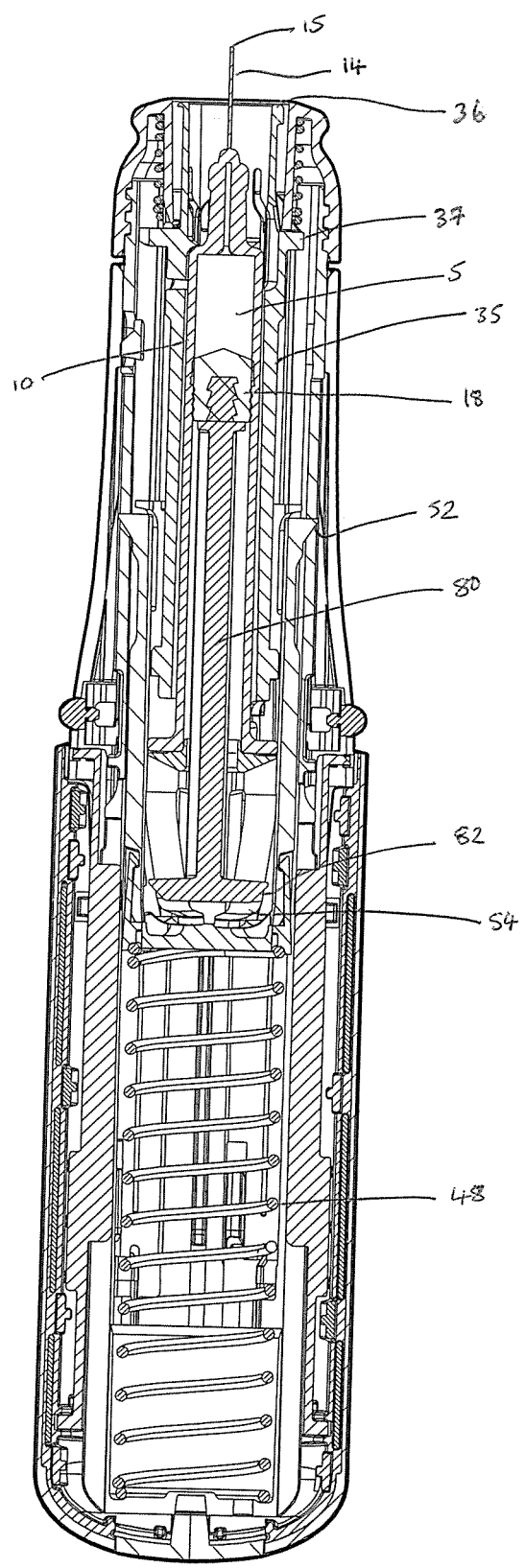

As a result of the decoupling of the drive shuttle 50 from the syringe carrier 35, all further forward drive experienced by the drive shuttle 50 is transferred to the plunger rod 80 by way of the 'hammer head' interaction of the inwardly flexed rear legs 54 thereof with the tapered head 82 of the plunger rod 80. The plunger rod 80 is therefore pushed down the syringe barrel 12 to exert axial force to the syringe stopper 18, the plunging movement of which results in expelling of the fluid contents 5 of the syringe 10 as shown in FIGS. 8D and 9D.

As the end of the injection stroke is reached, the rear legs 54 of the drive shuttle 50 flex outwards and are received within mid-slot 46 (see FIG. 3B) of the inner housing sleeve 40. The effect of this outwards-flexing is to bring the heads of the rear legs 54 out of engagement with the tapered drive head 82 of the plunger rod 80, thereby removing the 'hammer head' and decoupling the drive shuttle 50 from the plunger rod 80. The plunger rod 80 is then able to move axially within the inner housing sleeve 40 free from any influence of the drive spring 48.

Figure 8E:
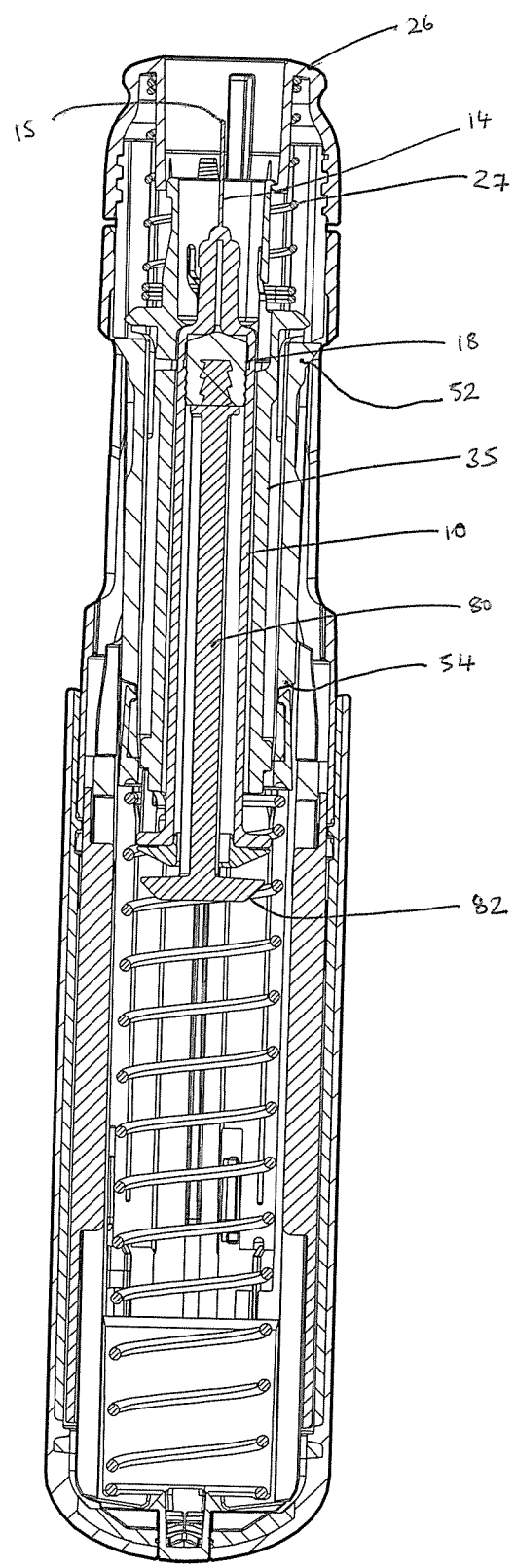
Figure 9E:
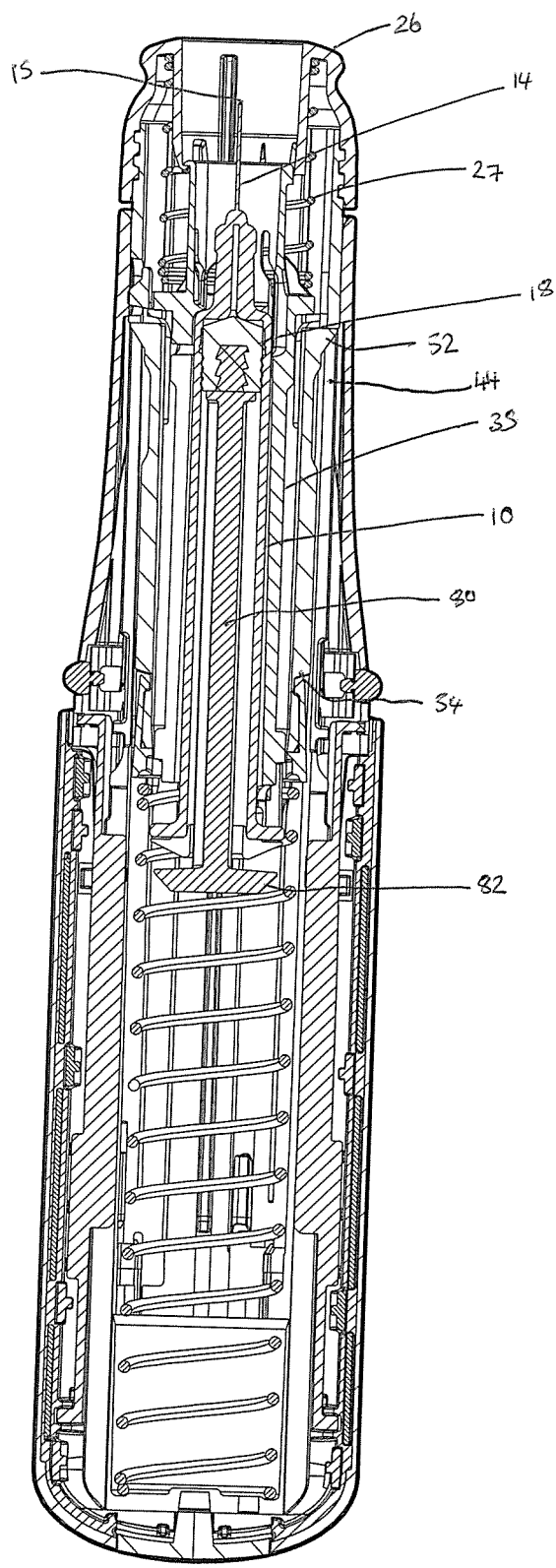

The syringe carrier 35 and syringe 10 carried thereby, now experience the return force of the earlier-compressed light return spring 27, which acts such as to move the syringe carrier 35 backwards to retract the syringe 10 to the 'end of use' position of FIGS. 8E and 9E, in which the tip 15 of the syringe needle 14 is again shrouded by the front housing part 26. The plunger rod head 82 passes through the rearward legs 54 of the drive shuttle 50 in this phase, the rear outward tags 54 having been deflected outwards into mid-slot 46 of the inner housing sleeve 40 to permit this. The syringe 10 is thus, effectively returned to its initial shrouded position, thereby removing any danger of possible inadvertent contact of the used needle 14, 15 with a user. Also in this 'end of injection' position, forward tags 52 of drive shuttle 50 seat up against a front ledge end of front slot 44 of the inner housing sleeve 40, thereby preventing any further forward movement of the drive shuttle 50. Typically, the device 1 is disposed of after use.

The auto-injector of the invention is suitable for the injected delivery of drug, particularly for the treatment and/or prophylaxis of a number of diseases, disorders or conditions, including infections (viral, e.g. HIV infection, bacterial, fungal and parasitic); endotoxic shock associated with infection; inflammatory diseases/autoimmunity such as osteoarthritis, rheumatoid arthritis, psoriatic arthritis, systemic lupus erythematosus (SLE), ankylosing spondilitis, COPD, asthma, Alzheimer's Disease, Crohn's disease, ulcerative colitis, irritable bowel syndrome and psoriasis; immune mediated inflammatory disorders of the central and peripheral nervous system such as multiple sclerosis and Guillain-Barr syndrome; graft-versus-host disease; organ transplant rejection; pain; cancer (including solid tumours such as melanomas, hepatoblastomas, sarcomas, squamous cell carcinomas, transitional cell cancers, ovarian cancers and hematologic malignancies, acute myelogenous leukaemia, chronic myelogenous leukemia, gastric cancer and colon cancer); congenital disorders, e.g. cystic fibrosis and sickle cell anaemia; growth disorders; epilepsy; treatment of infertility; heart disease including ischaemic diseases such as myocardial infarction as well as atherosclerosis and intravascular coagulation; bone disorders such as osteopenia and osteoporosis; and metabolic/idiopathic disease, e.g. diabetes.

In embodiments, the syringe of the auto-injector herein contains a liquid drug formulation, which is designed for refrigerated rest (e.g. at from 2-8° C.) and for injected delivery at room temperature (e.g. at or about 18-30° C.). In embodiments, the viscosity of the liquid drug formulation is less than 120 mPa·s (120 centipoise), in embodiments less than 100 mPa·s (100 centipoise) at a delivery temperature of 20° C.

Appropriate drugs may thus be selected from biologically active agents, including chemical entities, polysaccharides, steroids and, especially, naturally occurring and recombinant proteins, including glycoproteins, polypeptides and oligopeptides and polymeric derivatives thereof. Particular proteins, polypeptides and oligopeptides include hormones, such as insulin, epinephrine, norepinephrine, adrenocorticotrophin, somatotropin, erythropoietin and oxytocin; cytokines, such as lymphokines, chemokines and interleukins and receptors therefor, e.g. interleukin (IL)-1α, IL-1β, IL-1R, IL-2, IL-3, IL-4, IL-5, IL-6, IL-13, IL17, interferon (IFN)-α, IFN-β, IFN-γ, granulocyte monocyte colony stimulating factor, tumour necrosis factor-α; growth factors, such as nerve growth factor and platelet-derived growth factor; enzymes, such as tissue plasminogen activator; and, especially, immunoglobulins. Immunoglobulins include whole antibodies and functionally active fragments and/or derivatives thereof, for example polyclonal, monoclonal, recombinant, multi-valent, mono- or multi-specific, humanised or chimeric antibodies, single chain antibodies, Fab fragments, Fab' and F(ab')$_2$ fragments. Polymeric derivatives of such proteins, polypeptides and oligopeptides include derivatives formed between the protein, polypeptide or oligopeptide and a naturally occurring or synthetic polymer, e.g. a polysaccharide or a polyalylklene polymer such as a poly(ethyleneglycol) [PEG] or derivative thereof, e.g. methoxypoly (ethyleneglycol) [mPEG]. Particular agents include growth hormones and hormones for the treatment of infertility. Other particular agents are for the treatment of epilepsy such as brivaracetam and seletracetam.

The auto-injector device herein has been found to be of particular utility where the drug is an immunoglobulin or a fragment thereof, especially a PEGylated or mPEGylated antibody fragment.

The liquid drug formulations herein are typically aqueous formulations, which comprise the drug in solution and additionally other optional formulation components, which may include buffers (e.g. lactate, acetate), NaCl, and pH modifiers (e.g. NaOH).

The auto-injector device herein has been found to be of particular utility wherein the concentration of the drug (e.g. a therapeutic biologic type drug) in the liquid drug formulation is quite high. In particular, where the drug is a pegylated antibody the auto-injector device has been found to be of particular utility wherein the concentration of the drug is greater than 100 mg/ml, particularly greater than 150 mg/ml such as 200 mg/ml.

It is to be understood that the foregoing description is merely illustrative and is not to be limited to the details given herein. While several embodiments have been provided in the present disclosure, it should be understood that the disclosed systems, devices, and methods, and their components, may be embodied in many other specific forms without departing from the scope of the disclosure.

Variations and modifications will occur to those of skill in the art after reviewing this disclosure. The disclosed features may be implemented, in any combination and subcombinations (including multiple dependent combinations and subcombinations), with one or more other features described herein. The various features described or illustrated above, including any components thereof, may be combined or integrated in other systems. Moreover, certain features may be omitted or not implemented. Examples of changes, substitutions, and alterations are ascertainable by one skilled in the art and could be made without departing from the scope of the information disclosed herein. All references cited herein are incorporated by reference in their entirety and made part of this application.

The application of which this description and claims form part may be used as a basis for priority in respect of any subsequent application. The claims of such subsequent application may be directed to any feature or combination of features described herein. They may take the form of product, method or use claims and may include, by way of example and without limitation, one or more of the following claims.

The invention claimed is:

1. A housing part for an auto-injector comprising:
   a shell form body defining inner and outer shell surfaces;
   an over-coating, said over-coating covering at least part of said outer shell surface of said shell form body; and
   at least one window defined in the shell form body, wherein said over-coating extends into said at least one window,
   wherein a material forming the over-coating is softer than or is more compressible than a material forming the shell form body, and
   wherein the over-coating extends into the window beyond a depth of the inner shell surface to define an inwardly protruding element,
   wherein the inwardly protruding element is configured to be disposed between the shell form body and at least one functional element to be disposed within the housing part so as to provide impact protection for the at least one functional element within the housing part,
   wherein the inner shell surface adjacent the at least one window is free of said over-coating.

2. The housing part according to claim 1, wherein the over-coating is provided as an over-moulding to the shell form body.

3. The housing part according to claim 1, wherein the shell form body has a clam shell form.

4. The housing part according to claim 3, wherein the shell form body has a cylindrical or ellipsoidal clam shell form.

5. The housing part according to claim 1, wherein the housing part defines a rearward part of a housing for an auto-injector.

6. The housing part according to claim 5, wherein the at least one window is provided towards a rear end of the rearward part of the housing.

7. The housing part according to claim 1, wherein the shell form body comprises an acrylonitrile butadiene styrene material.

8. The housing part according to claim 1, wherein the over-coating comprises a thermoplastic elastomer material.

9. The housing part according to claim 8, wherein the thermoplastic elastomer material is selected from styrene-ethylene/butylene-styrene (SEBS) block copolymers, Styrene-Ethylene/Propylene-Styrene (SEPS) block copolymers, Styrene-Butadiene-Styrene (SBS) and thermoplastic vulcanisates (TPV) incorporating vulcanised rubber inclusions.

10. The housing part according to claim 1, wherein the over-coating is comprised of a material that has a hardness of from 20 Shore A to 60 Shore A.

11. An auto-injector device comprising the housing part according to claim 1, wherein said auto-injector device comprises a syringe.

12. The auto-injector according to claim 11, wherein the syringe contains a liquid drug formulation.

13. The auto-injector according to claim 12, wherein a barrel of said syringe has a volume corresponding to a single dose of said liquid drug formulation.

14. The auto-injector according to claim 13, wherein the liquid drug formulation comprises an aqueous formulation of a therapeutic biologic type drug.

15. The housing part according to claim 1, wherein the inwardly protruding element is configured to deform upon impact so as to provide impact protection for the at least one functional element to be disposed within the housing part.

16. The housing part according to claim 1, wherein the inwardly protruding element extends inwardly to only a partial depth of a cavity defined by the shell form body.

17. A housing part for an auto-injector comprising;
   a shell form body defining inner and outer shell surfaces, the shell form body forming a cavity for the disposition of one or more functional elements of the auto-injector within the housing part;
   an over-coating, said over-coating covering at least part of said outer shell surface of said shell form body and configured to provide impact protection to at least the shell form body;
   wherein a material forming the over-coating is softer than or is more compressible than a material forming the shell form body;
   at least one window defined in the shell form body, wherein a portion of said over-coating extends into said at least one window, the portion configured to enhance a bond between the over-coating and the shell form body;
   wherein the portion of said over-coating extends into the cavity away from and beyond a depth of the inner shell surface to define an inwardly protruding element;
   wherein the inwardly protruding element is configured to be disposed between the shell form body and at least one of said one or more functional elements disposed within the housing part so as to provide impact protection for the one or more functional elements within the housing part; and wherein the inwardly protruding element is not in direct contact with the inner shell surface, when the inwardly protruding element is not compressed.

18. A housing part for an auto-injector comprising:

a shell form body defining inner and outer shell surfaces and comprising at least one window defined in the shell form body;

an over-coating, the over-coating covering at least part of the outer shell surface of the shell form body and extending into the at least one window;

wherein the shell form body defines a cavity for the disposition of one or more functional elements of the auto-injector therein;

wherein a material forming the over-coating is softer than or is more compressible than a material forming the shell form body;

wherein the over-coating is configured to deform upon impact so as to provide impact protection to at least the shell form body;

a portion of the over-coating extends into the cavity to define an inwardly protruding element;

wherein the inwardly protruding element is configured to deform upon impact so as to provide additional impact protection to the one or more functional elements;

wherein the at least one window comprises a width, a length, and a depth; and wherein a width and a length of the inwardly protruding element are equal to or less than the respective width and the length of the at least one window.

* * * * *